United States Patent
Scheller

(10) Patent No.: US 10,828,191 B2
(45) Date of Patent: Nov. 10, 2020

(54) MICROSURGICAL INSTRUMENT TIP

(71) Applicant: Katalyst Surgical, LLC, Chesterfield, MO (US)

(72) Inventor: Gregg D Scheller, Wildwood, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 55 days.

(21) Appl. No.: 15/700,913

(22) Filed: Sep. 11, 2017

(65) Prior Publication Data
US 2017/0367884 A1    Dec. 28, 2017

Related U.S. Application Data

(62) Division of application No. 14/657,270, filed on Mar. 13, 2015, now Pat. No. 10,022,267.

(51) Int. Cl.
| | |
|---|---|
| *A61F 9/007* | (2006.01) |
| *A61B 17/29* | (2006.01) |
| *A61B 17/00* | (2006.01) |
| *A61B 17/30* | (2006.01) |

(52) U.S. Cl.
CPC .......... *A61F 9/00709* (2013.01); *A61B 17/29* (2013.01); *A61B 2017/00526* (2013.01); *A61B 2017/305* (2013.01); *Y10T 29/49789* (2015.01)

(58) Field of Classification Search
CPC ....... A61B 17/29; A61B 17/282; A61B 17/30; A61B 2017/00526; A61B 2017/305; A61B 2017/2904; A61B 2017/2945; A61B 2017/2901; A61B 17/28; A61B 2017/2825; A61F 9/00709; G04D 1/021
See application file for complete search history.

(56) References Cited

U.S. PATENT DOCUMENTS

| | | | |
|---|---|---|---|
| 1,371,288 | A | 3/1921 | Wolhaupter |
| 1,736,731 | A | 11/1929 | Breeding |
| 2,549,731 | A | 4/1951 | Wattley |
| 3,659,607 | A | 5/1972 | Banko |
| 4,135,868 | A | 1/1979 | Schainholz |
| 4,504,264 | A | 3/1985 | Kelman |
| 4,541,992 | A | 9/1985 | Jerge et al. |

(Continued)

FOREIGN PATENT DOCUMENTS

| | | |
|---|---|---|
| WO | WO1997015234 A1 | 5/1997 |
| WO | WO1998037819 A1 | 9/1998 |

(Continued)

OTHER PUBLICATIONS

Steve Charles, Techniques and tools for dissection of epiretinal membranes, Graefe' Arch Clin Exp Ophthalmol, 241:347-352, 2003.

(Continued)

*Primary Examiner* — Jocelin C Tanner

(57) ABSTRACT

An assembled blank may include a blank tip attached to a blank base, e.g., the blank tip may be welded to the blank base. The blank tip may be manufactured by modifying flat stock, e.g., tiers of blank tips may be manufactured by modifying tiers of flat stock. The blank tip may comprise a first forceps jaw, a second forceps jaw, and a blank tip aperture. The assembled blank may be disposed within a hypodermic tube and an actuation structure of a microsurgical instrument.

20 Claims, 19 Drawing Sheets

(56) References Cited

U.S. PATENT DOCUMENTS

| | | | |
|---|---|---|---|
| 4,553,957 A | 11/1985 | Williams et al. | |
| 4,610,252 A | 9/1986 | Catalano | |
| 4,706,666 A | 11/1987 | Sheets | |
| 4,739,761 A | 4/1988 | Grandon | |
| 4,761,028 A * | 8/1988 | Dulebohn | A61B 17/30 294/99.2 |
| 4,798,292 A | 1/1989 | Hauze | |
| 4,938,214 A * | 7/1990 | Specht | A61B 17/062 606/167 |
| 4,959,199 A | 9/1990 | Brewer | |
| 5,190,050 A | 3/1993 | Nitzsche | |
| 5,215,726 A | 6/1993 | Kudla et al. | |
| 5,222,973 A | 6/1993 | Sharpe et al. | |
| 5,227,313 A | 7/1993 | Gluck et al. | |
| 5,286,255 A | 2/1994 | Webber | |
| 5,318,589 A | 6/1994 | Lichtman | |
| 5,346,677 A | 9/1994 | Risk | |
| 5,355,871 A | 10/1994 | Hurley et al. | |
| 5,370,658 A | 12/1994 | Scheller et al. | |
| 5,384,103 A | 1/1995 | Miller | |
| 5,415,645 A | 5/1995 | Friend et al. | |
| 5,425,730 A | 6/1995 | Luloh | |
| 5,433,929 A | 7/1995 | Riihimaki et al. | |
| 5,451,230 A | 9/1995 | Steinert | |
| 5,527,313 A | 6/1996 | Scott et al. | |
| 5,601,581 A | 2/1997 | Fogarty et al. | |
| 5,636,639 A | 6/1997 | Turturro et al. | |
| 5,647,115 A * | 7/1997 | Slater | A61B 10/0266 29/557 |
| 5,695,514 A | 12/1997 | Chin | |
| D393,067 S | 3/1998 | Geary et al. | |
| D393,715 S | 4/1998 | Strickland | |
| 5,759,502 A | 6/1998 | Spencer et al. | |
| 5,792,165 A | 8/1998 | Klieman et al. | |
| 5,810,811 A | 9/1998 | Yates et al. | |
| 5,843,387 A | 12/1998 | Dane et al. | |
| 5,851,197 A | 12/1998 | Marano et al. | |
| 5,893,873 A | 4/1999 | Rader et al. | |
| 5,893,877 A | 4/1999 | Gampp, Jr. et al. | |
| 5,913,422 A | 6/1999 | Cote et al. | |
| 5,916,159 A | 6/1999 | Ryan, Jr. | |
| 5,921,998 A | 7/1999 | Tano et al. | |
| 6,099,550 A | 8/2000 | Yoon | |
| 6,159,162 A | 12/2000 | Kostylev et al. | |
| 6,183,467 B1 | 2/2001 | Shapeton et al. | |
| 6,277,100 B1 | 8/2001 | Raulerson et al. | |
| D453,222 S | 1/2002 | Garito et al. | |
| 6,419,675 B1 | 7/2002 | Gallo, Sr. | |
| D463,555 S | 9/2002 | Etter et al. | |
| 6,451,037 B1 | 9/2002 | Chandrasekaran et al. | |
| 6,488,695 B1 | 12/2002 | Hickingbotham | |
| 6,551,129 B2 | 4/2003 | Kato | |
| 6,572,565 B2 | 6/2003 | Daley et al. | |
| 6,575,989 B1 | 6/2003 | Scheller et al. | |
| 6,616,683 B1 | 9/2003 | Toth et al. | |
| 6,730,076 B2 | 5/2004 | Hickingbotham | |
| 6,749,601 B2 | 6/2004 | Chin | |
| 6,772,765 B2 | 8/2004 | Scheller et al. | |
| 6,800,076 B2 | 10/2004 | Humayun | |
| 6,863,668 B2 | 3/2005 | Gillespie et al. | |
| 6,908,476 B2 | 6/2005 | Jud et al. | |
| 6,926,728 B2 | 8/2005 | Zucherman et al. | |
| 6,945,984 B2 | 9/2005 | Arumi et al. | |
| 7,338,494 B2 | 3/2008 | Ryan | |
| D565,733 S | 4/2008 | Andre | |
| 7,438,717 B2 | 10/2008 | Tylke | |
| 7,632,242 B2 | 12/2009 | Griffin et al. | |
| 7,731,728 B2 | 6/2010 | Glaser | |
| 7,783,346 B2 | 8/2010 | Smith et al. | |
| D625,412 S | 10/2010 | Garito et al. | |
| 7,766,904 B2 | 10/2010 | Mc Gowan, Sr. et al. | |
| 7,935,080 B2 | 5/2011 | Howell et al. | |
| 8,038,692 B2 | 10/2011 | Valencia et al. | |
| 8,197,468 B2 | 6/2012 | Scheller et al. | |
| 8,202,288 B2 | 6/2012 | Ryan | |
| 8,262,682 B2 * | 9/2012 | Terao | A61B 17/3211 606/128 |
| 8,821,444 B2 | 9/2014 | Scheller et al. | |
| 9,138,346 B2 | 9/2015 | Scheller et al. | |
| 9,149,389 B2 | 10/2015 | Scheller et al. | |
| 9,204,995 B2 | 12/2015 | Scheller et al. | |
| 9,226,762 B2 | 1/2016 | Scheller et al. | |
| 9,427,251 B2 | 8/2016 | Rethy et al. | |
| 2001/0056286 A1 | 12/2001 | Etter et al. | |
| 2002/0115902 A1 | 8/2002 | Dejuan, Jr. et al. | |
| 2003/0171762 A1 | 9/2003 | Forchette et al. | |
| 2003/0229976 A1 | 12/2003 | Scheller et al. | |
| 2005/0154403 A1 | 7/2005 | Sauer et al. | |
| 2005/0245950 A1 | 11/2005 | Kozlowski | |
| 2006/0036270 A1 | 2/2006 | Terao | |
| 2006/0235382 A1 | 10/2006 | Cohen et al. | |
| 2007/0104609 A1 | 5/2007 | Powell | |
| 2007/0106246 A1 | 5/2007 | Modesitt | |
| 2007/0185514 A1 | 8/2007 | Kirchhevel | |
| 2007/0282348 A1 | 12/2007 | Lumpkin | |
| 2008/0183199 A1 | 7/2008 | Attinger | |
| 2008/0195135 A1 | 8/2008 | Attinger | |
| 2008/0200923 A1 * | 8/2008 | Beckman | A61F 9/00781 606/108 |
| 2008/0255526 A1 | 10/2008 | Bosse et al. | |
| 2009/0030427 A1 | 1/2009 | Razvi et al. | |
| 2009/0112258 A1 | 4/2009 | Kreidler | |
| 2009/0131870 A1 | 5/2009 | Fiser | |
| 2009/0228066 A1 | 10/2009 | Hirata et al. | |
| 2009/0318856 A1 | 12/2009 | Glaser | |
| 2010/0023050 A1 | 1/2010 | Reinauer et al. | |
| 2010/0028605 A1 * | 2/2010 | Oshima | H01L 21/02021 428/156 |
| 2010/0063359 A1 | 3/2010 | Okoniewski | |
| 2010/0145381 A1 | 6/2010 | Moon | |
| 2010/0228226 A1 | 9/2010 | Nielsen | |
| 2011/0015669 A1 | 1/2011 | Corcosteugi | |
| 2012/0116361 A1 | 5/2012 | Hanlon et al. | |
| 2012/0150216 A1 | 6/2012 | Hickingbotham et al. | |
| 2012/0179172 A1 | 7/2012 | Paul, Jr. et al. | |
| 2012/0191120 A1 | 7/2012 | Linsi | |
| 2013/0071507 A1 | 3/2013 | Scheller et al. | |
| 2013/0085326 A1 | 4/2013 | Scheller et al. | |
| 2013/0197488 A1 | 8/2013 | Scheller et al. | |
| 2014/0012314 A1 | 1/2014 | Dai et al. | |
| 2014/0066977 A1 | 3/2014 | Scheller et al. | |
| 2014/0121697 A1 * | 5/2014 | Scheller | A61B 17/30 606/207 |
| 2014/0128909 A1 | 5/2014 | Scheller et al. | |
| 2014/0135820 A1 | 5/2014 | Schaller et al. | |
| 2014/0142603 A1 | 5/2014 | Scheller et al. | |
| 2014/0163363 A1 | 6/2014 | Scheller et al. | |
| 2014/0172010 A1 | 6/2014 | Vezzu | |
| 2014/0277110 A1 | 9/2014 | Scheller et al. | |
| 2015/0088193 A1 | 3/2015 | Scheller et al. | |
| 2015/0173944 A1 | 6/2015 | Linsi et al. | |

FOREIGN PATENT DOCUMENTS

| | | |
|---|---|---|
| WO | WO2002041796 A2 | 5/2002 |
| WO | WO2017066026 A1 | 4/2017 |

OTHER PUBLICATIONS http://www.bpf.co.uk/plastipedia/polymers/polyamides.aspx [Mar. 20, 2017 4:57:01 PM].

* cited by examiner

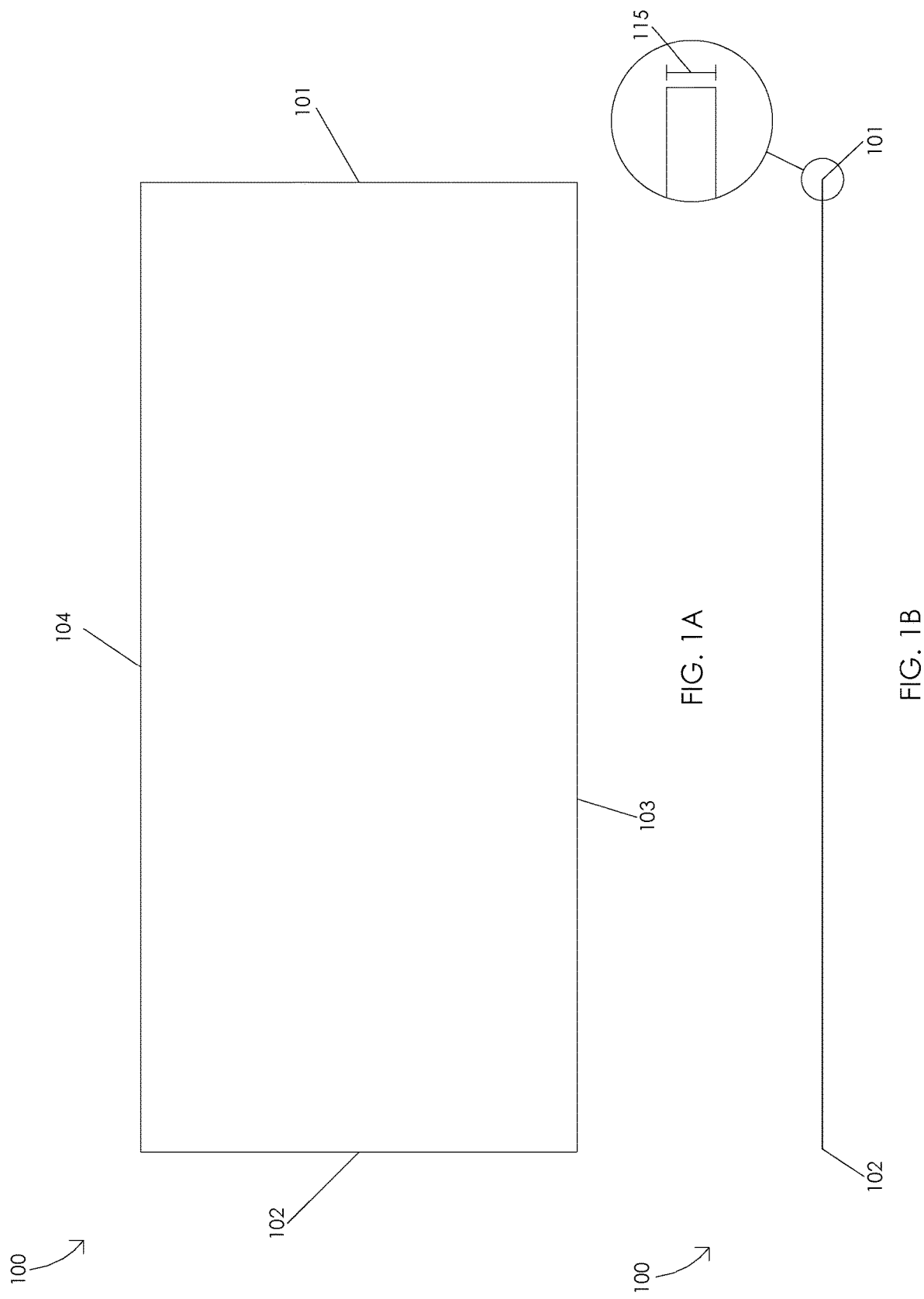

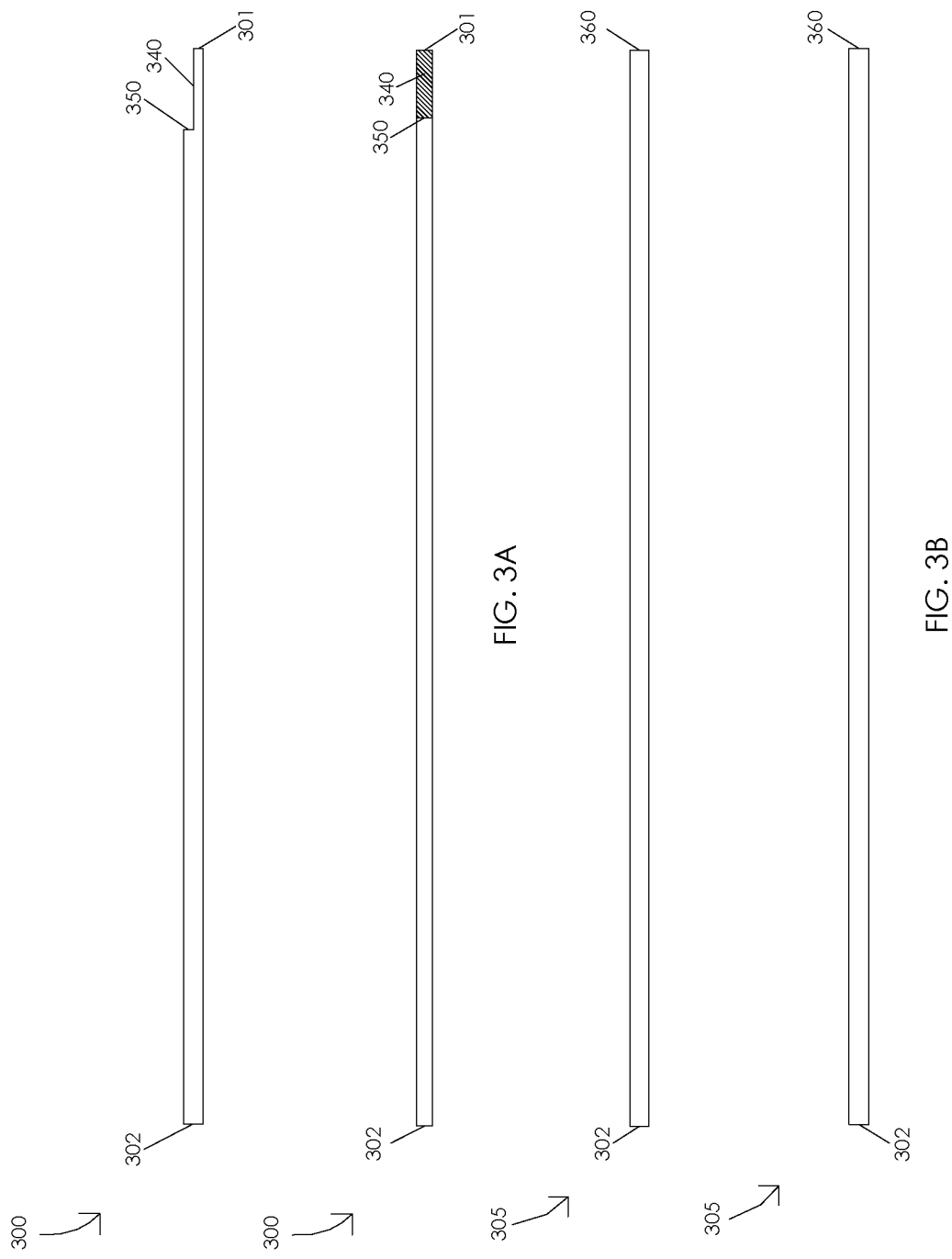

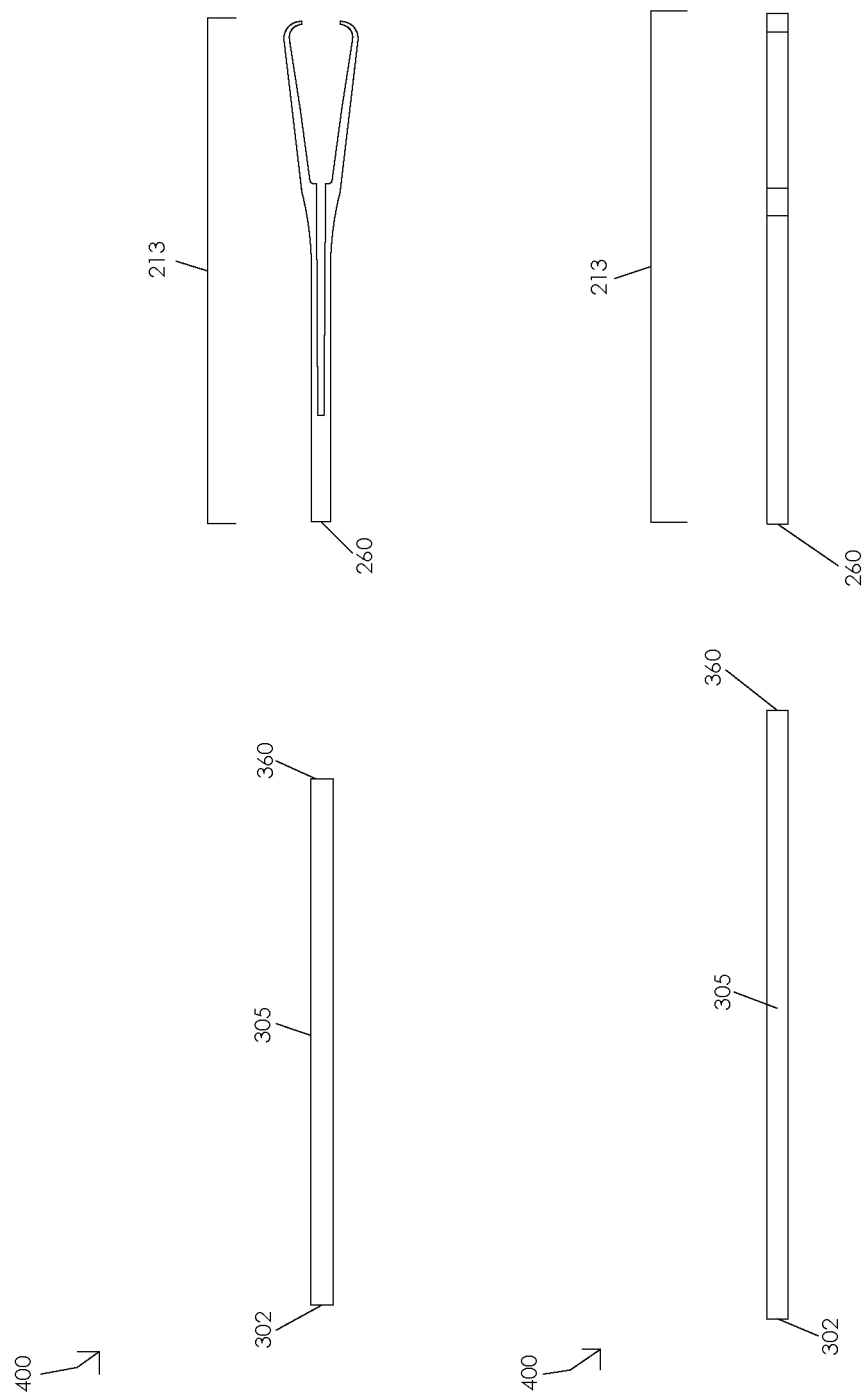

MICROSURGICAL INSTRUMENT TIP

CROSS-REFERENCE TO RELATED APPLICATIONS

This application is a divisional of prior application Ser. No. 14/657,270, filed Mar. 13, 2015.

FIELD OF THE INVENTION

The present disclosure relates to a surgical instrument, and, more particularly, to a microsurgical instrument tip.

BACKGROUND OF THE INVENTION

Microsurgical instrument tips are commonly manufactured from metal blanks. A metal blank is a thin, elongate wire having a block portion at one end. Metal blanks are typically custom manufactured by a first specialized machinist operating a first piece of capital equipment, e.g., a CNC machinist operating a Swiss-style lathe. After a metal blank is manufactured, the metal blank is modified by a second specialized machinist operating a second piece of capital equipment, e.g., an EDM machinist operating an electrical discharge machine. Metal blanks are modified into microsurgical instrument tips one metal blank at a time, e.g., an EDM machinist operating an electrical discharge machine manufactures a first microsurgical instrument tip from a first metal blank and then the EDM machinist manufactures a second microsurgical instrument tip from a second metal blank.

BRIEF SUMMARY OF THE INVENTION

In one or more embodiments, an assembled blank may comprise a blank tip attached to a blank base, e.g., the blank tip may be welded to the blank base. Illustratively, the blank tip may be manufactured by modifying flat stock, e.g., tiers of blank tips may be manufactured by modifying tiers of flat stock. In one or more embodiments, the blank tip may comprise a first forceps jaw, a second forceps jaw, and a blank tip aperture. Illustratively, the assembled blank may be disposed within a hypodermic tube and an actuation structure of a microsurgical instrument.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a flat stock;

FIGS. 3A and 3B are schematic diagrams illustrating a blank base;

FIGS. 4A, 4B, 4C, and 4D are schematic diagrams illustrating exploded views of a blank assembly;

DETAILED DESCRIPTION OF AN ILLUSTRATIVE EMBODIMENT

Figure 2A:
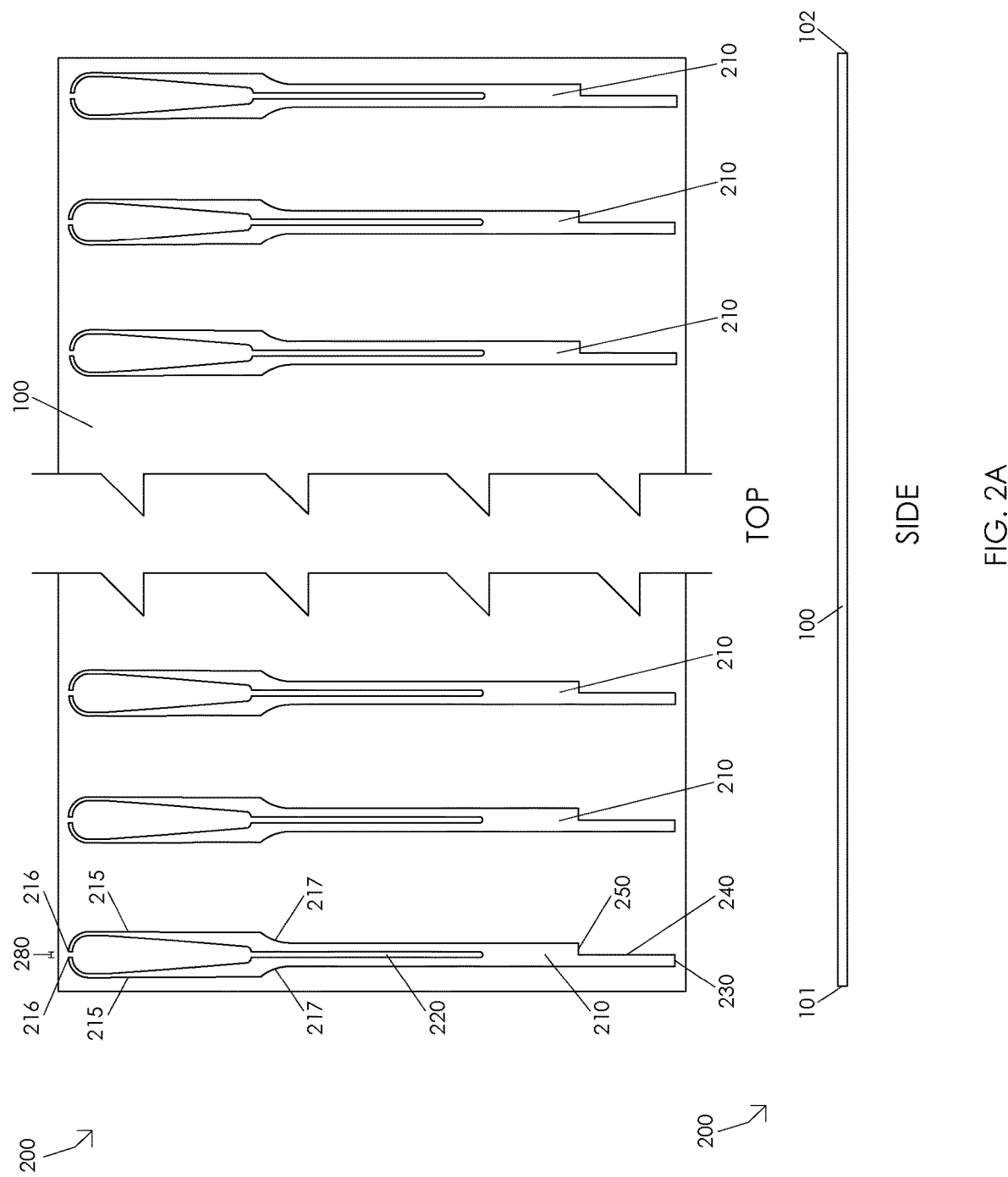
FIGS. 2A, 2B, 2C, 2D, 2E, 2F, 2G and 2H are schematic diagrams illustrating a modified flat stock.

FIGS. 1A and 1B are schematic diagrams illustrating a flat stock 100. FIG. 1A illustrates a top view of flat stock 100. Illustratively, flat stock 100 may comprise a flat stock distal end 101, a flat stock proximal end 102, a flat stock dorsal end 103, and a flat stock ventral end 104. FIG. 1B illustrates a side view of flat stock 100. In one or more embodiments, flat stock 100 may comprise a flat stock thickness 115. Illustratively, flat stock thickness 115 may be a distance in a range of 0.005 to 0.013 inches, e.g., flat stock thickness 115 may be a distance of 0.008 inches. In one or more embodiments, flat stock thickness 115 may be a distance of less than 0.005 inches or greater than 0.013 inches. Illustratively, flat stock thickness 115 may be a specific distance corresponding to a particular size of microsurgical instrument. In one or more embodiments, flat stock thickness 115 may be a distance in a range of 0.007 to 0.009 inches for a 25 gauge ophthalmic surgical forceps, e.g., flat stock thickness 115 may be a distance of 0.008 inches for a 25 gauge ophthalmic surgical forceps. Illustratively, flat stock thickness 115 may be a distance in a range of 0.011 to 0.013 inches for a 23 gauge ophthalmic surgical forceps, e.g., flat stock thickness 115 may be a distance of 0.012 inches for a 23 gauge ophthalmic surgical forceps. In one or more embodiments, flat stock 100 may be manufactured from any suitable material, e.g., polymers, metals, metal alloys, etc., or from any combination of suitable materials. Illustratively, flat stock 100 may be manufactured from stainless steel, e.g., flat stock 100 may be manufactured from 17-7 PH Stainless Steel Condition C.

FIGS. 2A, 2B, 2C, 2D, 2E, 2F, 2G and 2H are schematic diagrams illustrating a modified flat stock 200. FIG. 2A illustrates modified flat stock 200 to manufacture a closed step blank tip 210. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of closed step blank tips 210, e.g., flat stock 100 may be actuated relative to a tool electrode of an electrical discharge machine to cut out a plurality of closed step blank tips 210. For example, flat stock 100 may be disposed in a plane perpendicular to a tool electrode of an electrical discharge machine and then flat stock 100 may be actuated relative to the tool electrode to cut out a plurality of closed step blank tips 210. Illustratively, closed step blank tip 210 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, a blank base shoulder interface 230, a blank base interface 240, and a blank tip shoulder 250. In one or more embodiments, first forceps jaw distal end 216 and second forceps jaw distal end 216 may be separated by a closed jaw separation distance 280. Illustratively, closed jaw separation distance 280 may be a distance in a range of 0.001 to 0.005 inches, e.g., closed jaw separation distance 280 may be a distance of 0.003 inches. In one or more embodiments, closed jaw separation distance 280 may be a distance of less than 0.001 inches or greater than 0.005 inches.

Figure 2B:
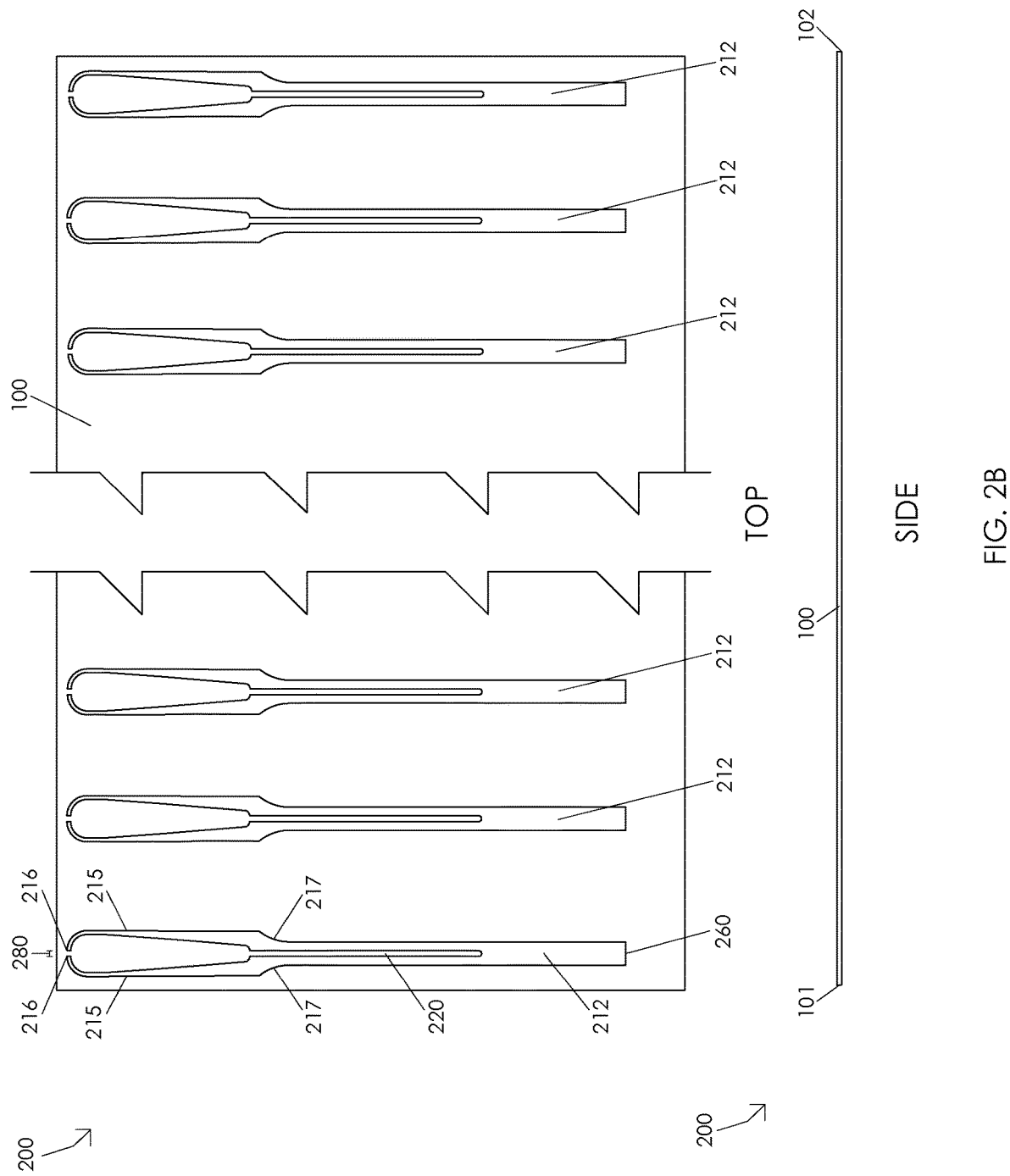

FIG. 2B illustrates modified flat stock 200 to manufacture a closed blunt blank tip 212. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of closed blunt blank tips 212, e.g., flat stock 100 may be actuated relative to a tool electrode of an electrical discharge machine to cut out a plurality of closed blunt blank tips 212. For example, flat stock 100 may be disposed in a plane perpendicular to a tool electrode of an electrical discharge machine and then flat stock 100 may be actuated relative to the tool electrode to cut out a plurality of closed blunt blank tips 212. Illustratively, closed blunt blank tip 212 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, and a blunt blank base interface 260. In one or more embodiments, first forceps jaw distal end 216 and second forceps jaw distal end 216 may be separated by a closed jaw separation distance 280. Illustratively, closed jaw separation distance 280 may be a distance in a range of 0.001 to 0.005 inches, e.g., closed jaw separation distance 280 may be a distance of 0.003 inches. In one or more embodiments, closed jaw separation distance 280 may be a distance of less than 0.001 inches or greater than 0.005 inches.

Figure 2C:
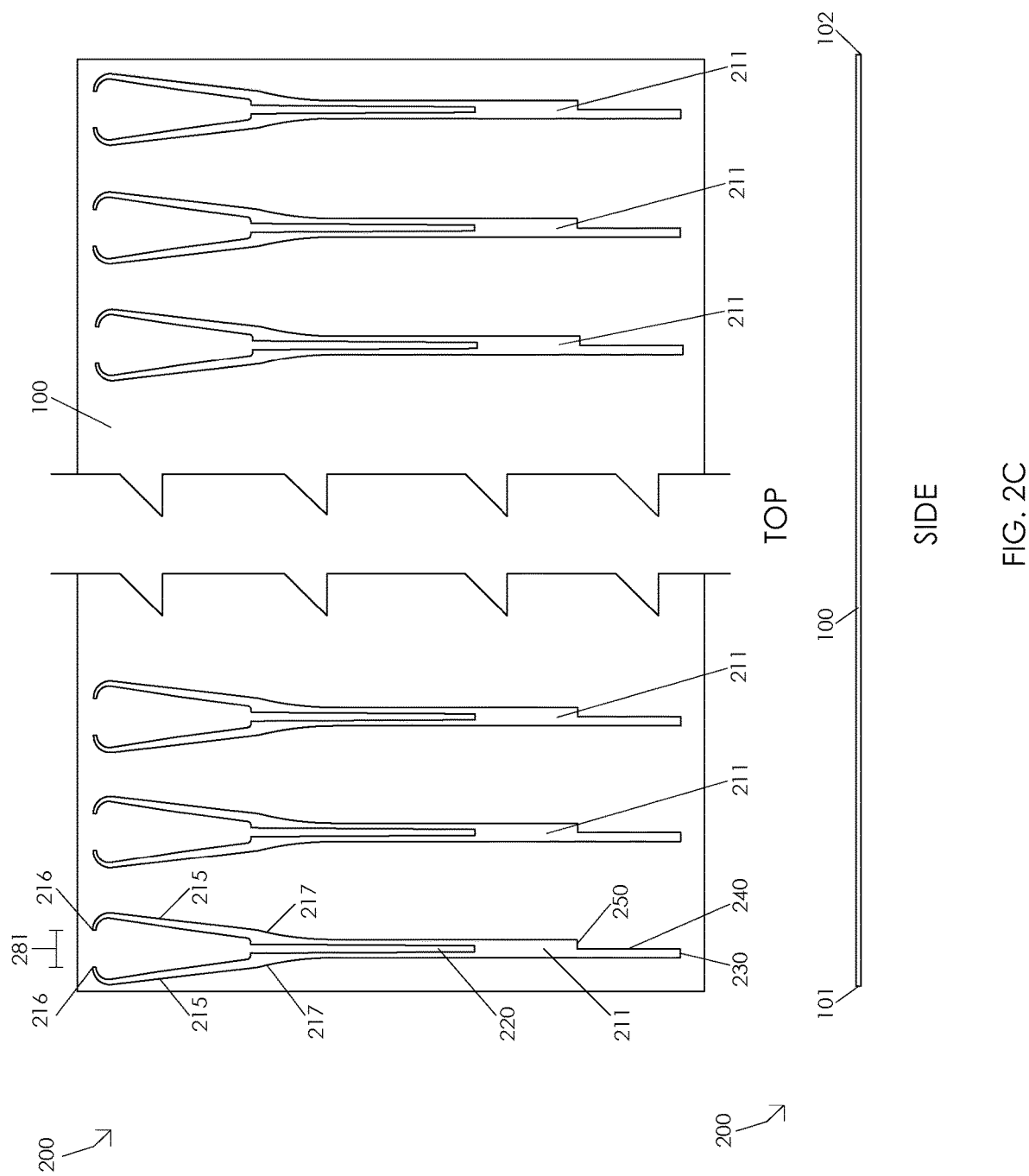

FIG. 2C illustrates modified flat stock 200 to manufacture an open step blank tip 211. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of open step blank tips 211, e.g., flat stock 100 may be actuated relative to a tool electrode of an electrical discharge machine to cut out a plurality of open step blank tips 211. For example, flat stock 100 may be disposed in a plane perpendicular to a tool electrode of an electrical discharge machine and then flat stock 100 may be actuated relative to the tool electrode to cut out a plurality of open step blank tips 211. Illustratively, open step blank tip 211 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, a blank base shoulder interface 230, a blank base interface 240, and a blank tip shoulder 250. In one or more embodiments, first forceps jaw distal end 216 and second forceps jaw distal end 216 may be separated by an open jaw separation distance 281. Illustratively, open jaw separation distance 281 may be a distance in a range of 0.010 to 0.050 inches, e.g., open jaw separation distance 281 may be a distance of 0.038 inches. In one or more embodiments, open jaw separation distance 281 may be a distance of less than 0.010 inches or greater than 0.050 inches. Illustratively, open jaw separation distance 181 may be a specific distance corresponding to a particular size of microsurgical instrument. In one or more embodiments, open jaw separation distance 181 may be a distance in a range of 0.025 to 0.035 inches for a 25 gauge ophthalmic surgical forceps, e.g., open jaw separation distance 181 may be a distance of 0.030 inches for a 25 gauge ophthalmic surgical forceps. Illustratively, open jaw separation distance 181 may be a distance in a range of 0.030 to 0.045 inches for a 23 gauge ophthalmic surgical forceps, e.g., open jaw separation distance 181 may be a distance of 0.038 inches for a 23 gauge ophthalmic surgical forceps.

Figure 2D:
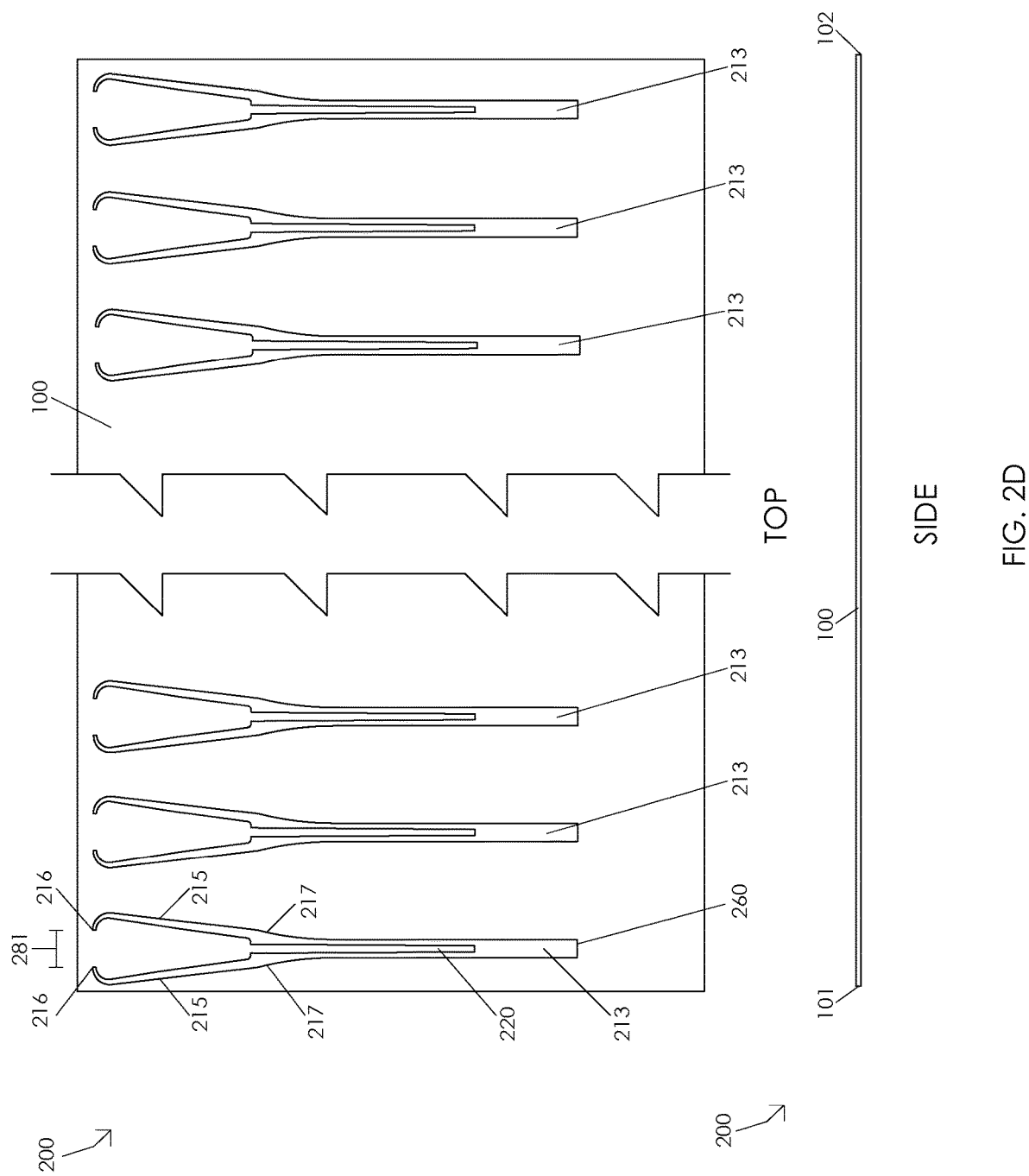

FIG. 2D illustrates modified flat stock 200 to manufacture an open blunt blank tip 213. Illustratively, modified flat stock 200 may comprise flat stock 100 modified by cutting predefined patterns into flat stock 100, e.g., modified flat stock 200 may comprise flat stock 100 cut by a laser ablation, an electrical discharge machine, a water jet, a drill, etc. In one or more embodiments, modified flat stock 200 may comprise a plurality of open blunt blank tips 213, e.g., flat stock 100 may be actuated relative to a tool electrode of an electrical discharge machine to cut out a plurality of open blunt blank tips 213. For example, flat stock 100 may be disposed in a plane perpendicular to a tool electrode of an electrical discharge machine and then flat stock 100 may be actuated relative to the tool electrode to cut out a plurality of open blunt blank tips 213. Illustratively, open blunt blank tip 213 may comprise a first forceps jaw 215 having a first forceps jaw distal end 216 and a first forceps jaw proximal end 217, a second forceps jaw 215 having a second forceps jaw distal end 216 and a second forceps jaw proximal end 217, a blank tip aperture 220, and a blunt blank base interface 260. In one or more embodiments, first forceps jaw distal end 216 and second forceps jaw distal end 216 may be separated by an open jaw separation distance 281. Illustratively, open jaw separation distance 281 may be a distance in a range of 0.010 to 0.050 inches, e.g., open jaw separation distance 281 may be a distance of 0.038 inches. In one or more embodiments, open jaw separation distance 281 may be a distance of less than 0.010 inches or greater than 0.050 inches. Illustratively, open jaw separation distance 181 may be a specific distance corresponding to a particular size of microsurgical instrument. In one or more embodiments, open jaw separation distance 181 may be a distance in a range of 0.025 to 0.035 inches for a 25 gauge ophthalmic surgical forceps, e.g., open jaw separation distance 181 may be a distance of 0.030 inches for a 25 gauge ophthalmic surgical forceps. Illustratively, open jaw separation distance 181 may be a distance in a range of 0.030 to 0.045 inches for a 23 gauge ophthalmic surgical forceps, e.g., open jaw separation distance 181 may be a distance of 0.038 inches for a 23 gauge ophthalmic surgical forceps.

Figure 2E:
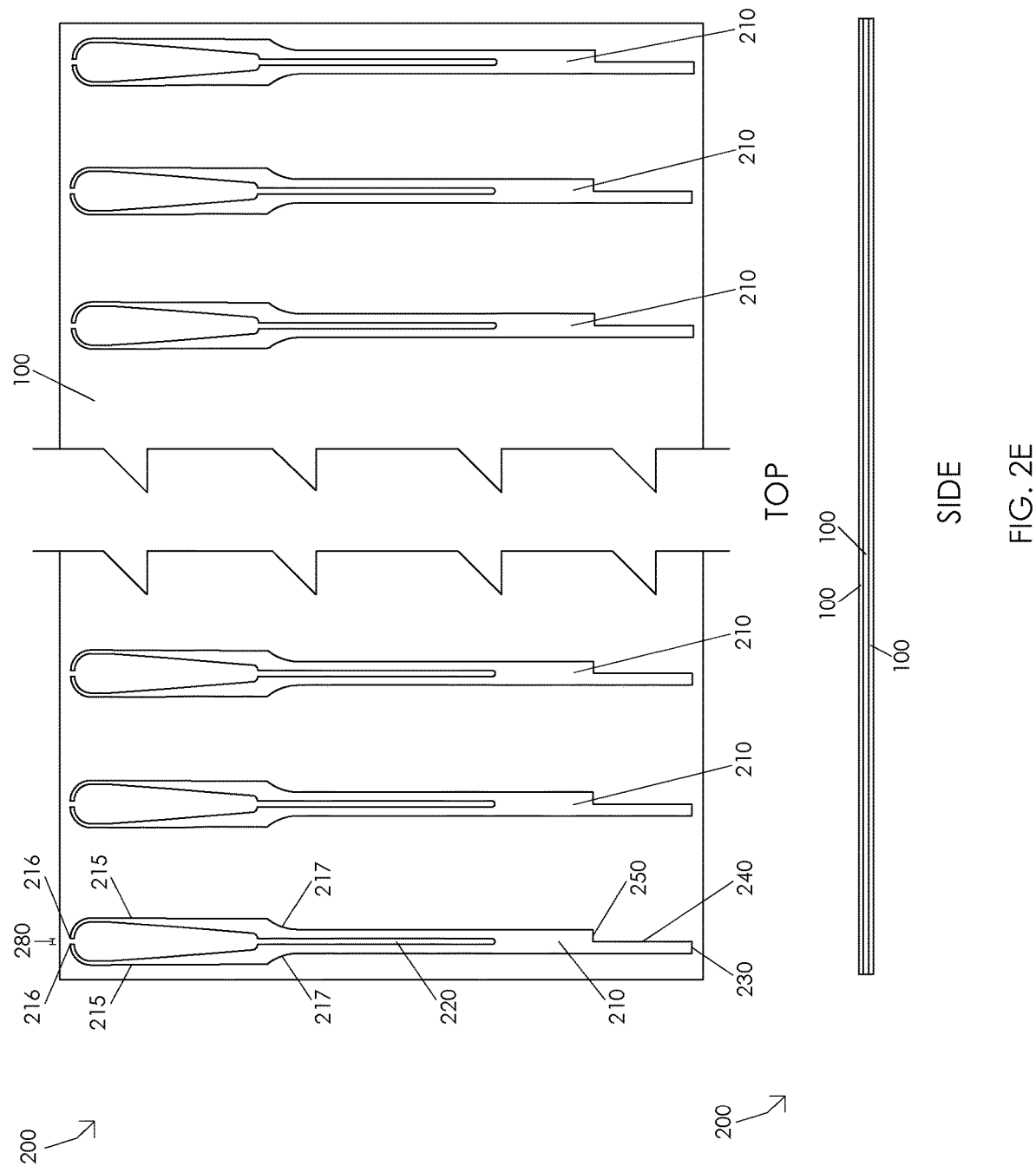

FIG. 2E illustrates modified flat stock 200 to manufacture a plurality of closed step blank tips 210 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of closed step blank tips 210, e.g., tiers of flat stock 100 may be actuated relative to a tool electrode of an electrical discharge machine to cut out a plurality of tiers of closed step blank tips 210. For example, tiers of flat stock 100 may be disposed in a plane perpendicular to a tool electrode of an electrical discharge machine and then tiers of flat stock 100 may be actuated relative to the tool electrode to cut out a plurality of closed step blank tips 210.

Figure 2F:
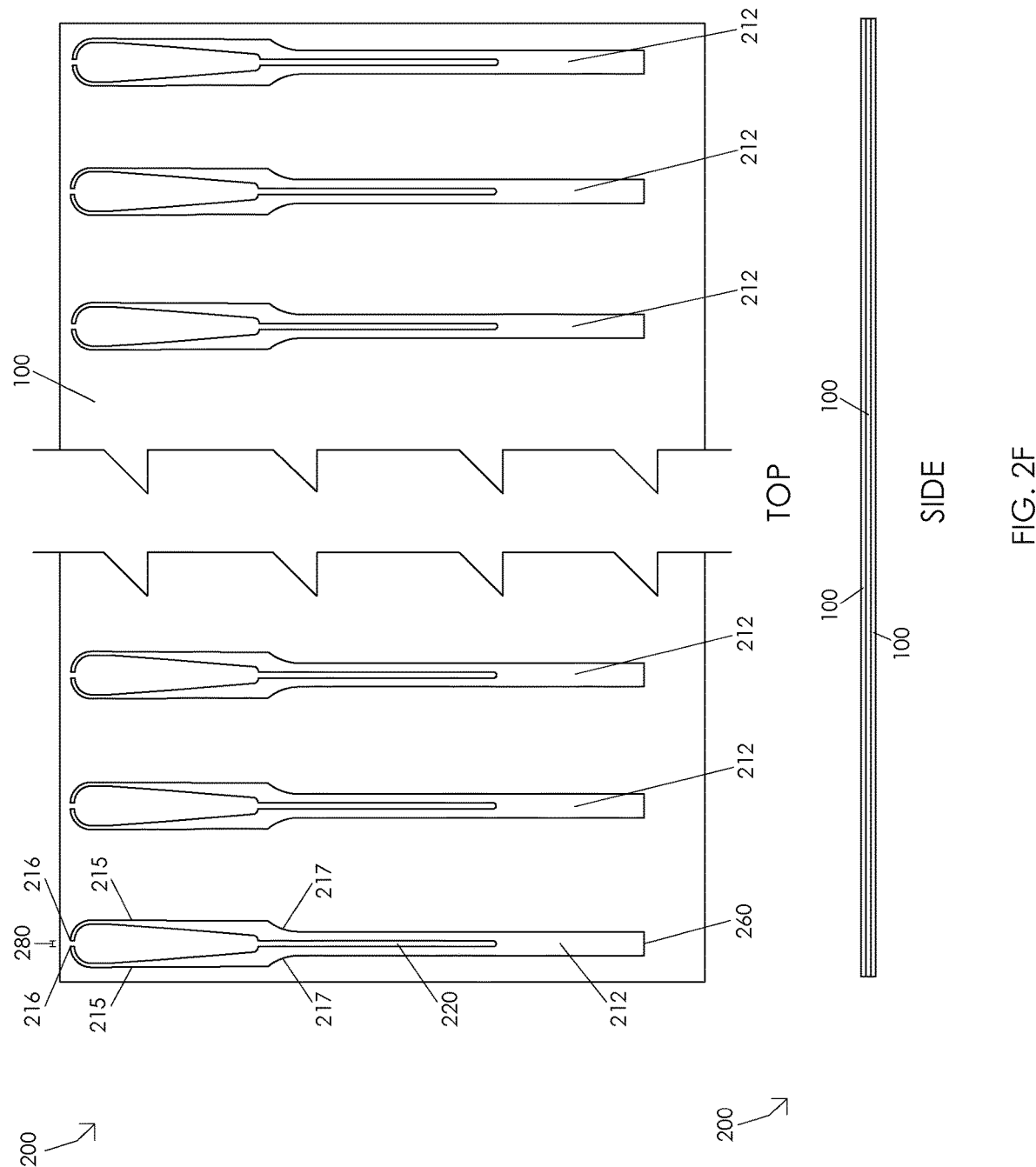

FIG. 2F illustrates modified flat stock 200 to manufacture a plurality of closed blunt blank tips 212 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of closed blunt blank tips 212, e.g., tiers of flat stock 100 may be actuated relative to a tool electrode of an electrical discharge machine to cut out a plurality of tiers of closed blunt blank tips 212. For example, tiers of flat stock 100 may be disposed in a plane perpendicular to a tool electrode of an electrical discharge machine and then tiers of flat stock 100 may be actuated relative to the tool electrode to cut out a plurality of closed blunt blank tips 212.

Figure 2G:
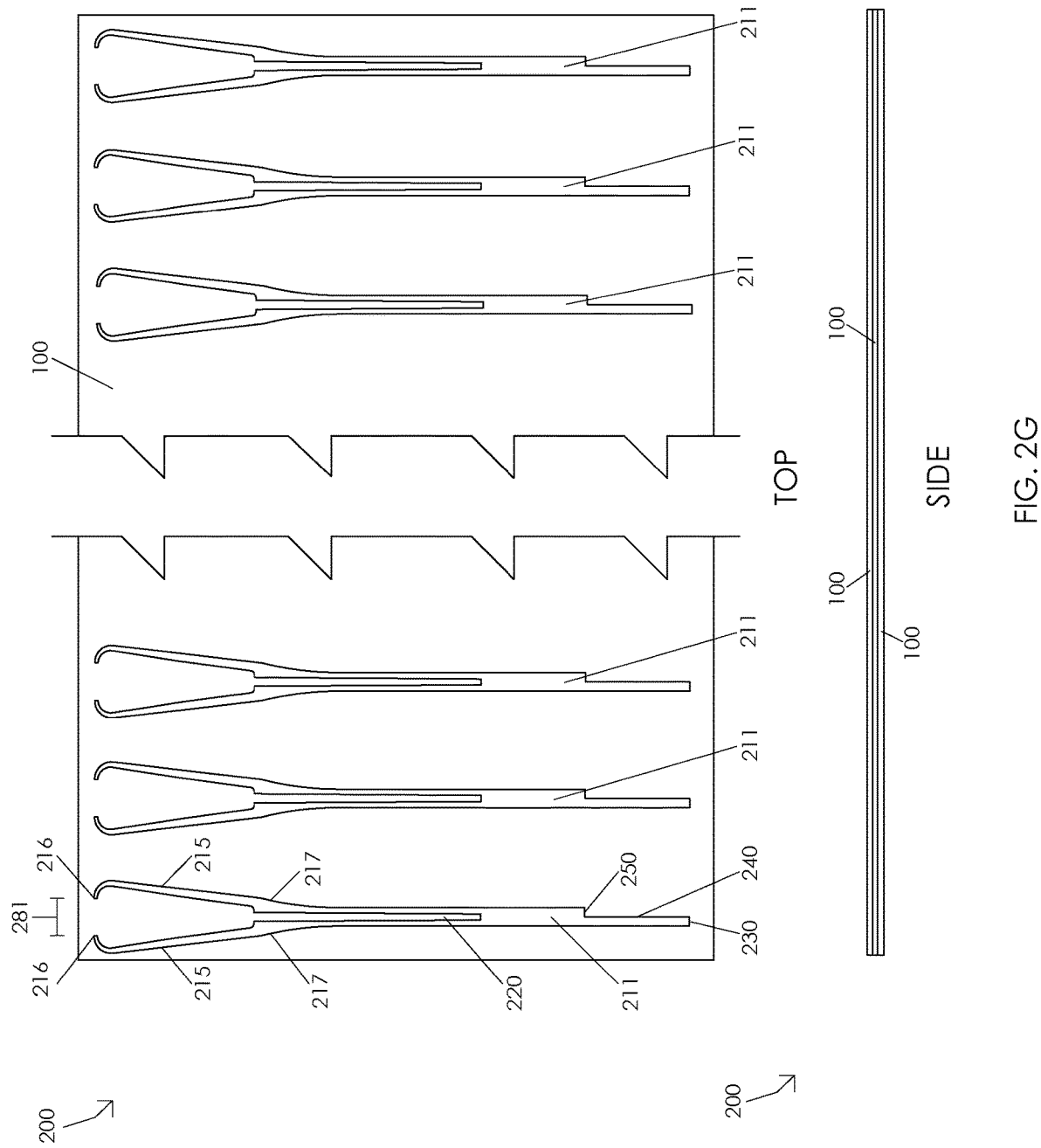

FIG. 2G illustrates modified flat stock 200 to manufacture a plurality of open step blank tips 211 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of open step blank tips 211, e.g., tiers of flat stock 100 may be actuated relative to a tool electrode of an electrical discharge machine to cut out a plurality of tiers of open step blank tips 211. For example, tiers of flat stock 100 may be disposed in a plane perpendicular to a tool electrode of an electrical discharge machine and then tiers of flat stock 100 may be actuated relative to the tool electrode to cut out a plurality of open step blank tips 211.

Figure 2H:
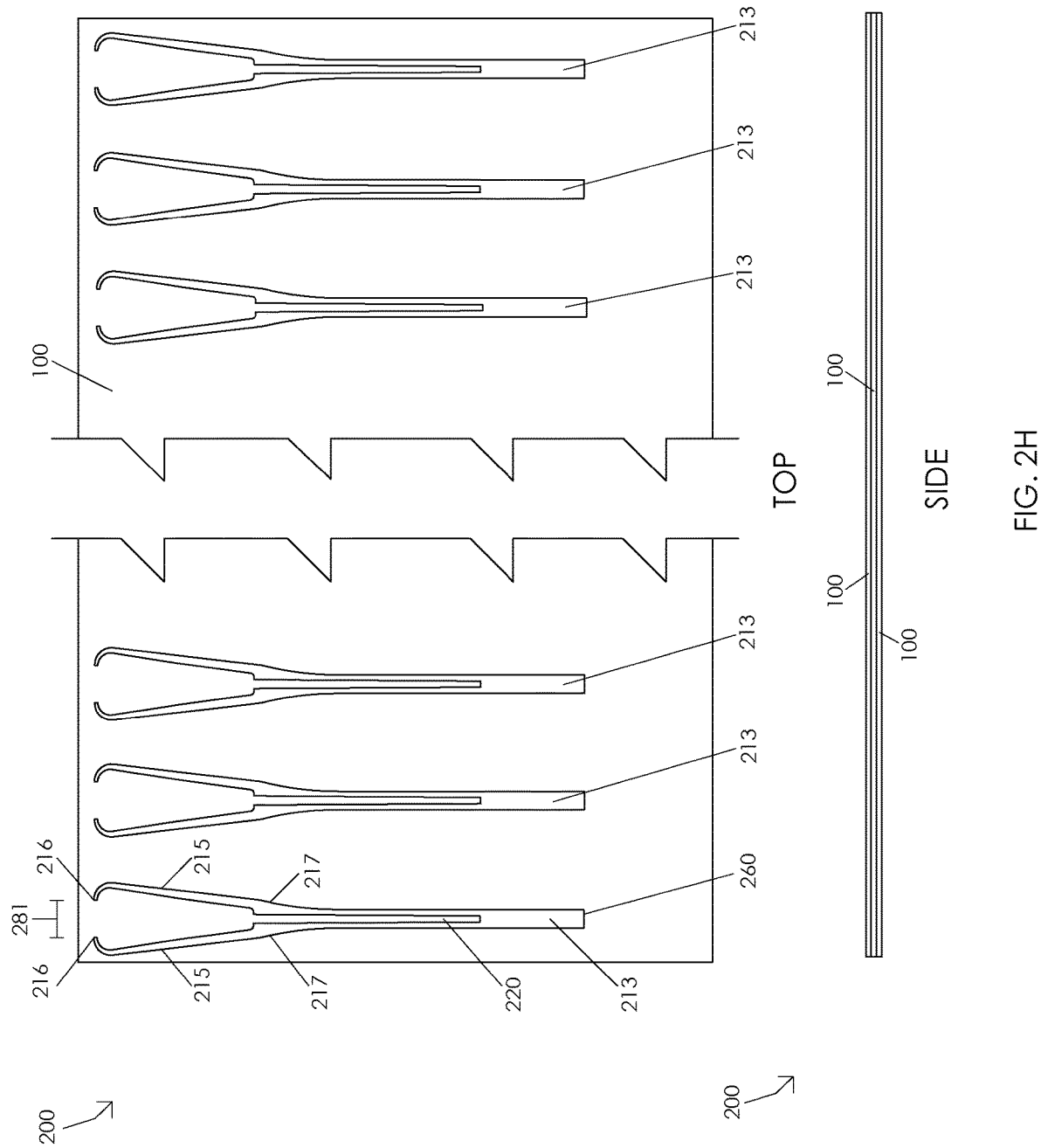

FIG. 2H illustrates modified flat stock 200 to manufacture a plurality of open blunt blank tips 213 in tiers. In one or more embodiments, a first flat stock 100 may be disposed over a second flat stock 100 and the first flat stock 100 and the second flat stock 100 may be simultaneously modified by cutting predefined patterns into the first flat stock 100 and the second flat stock 100. Illustratively, modified flat stock 200 may comprise a first flat stock 100 disposed over a second flat stock 100 wherein the first flat stock 100 and the second flat stock 100 are modified by cutting predefined patterns into the first flat stock 100 and the second flat stock 100, e.g., modified flat stock 200 may comprise a first flat stock 100 and a second flat stock 100 cut by a laser ablation, an electrical discharge machine, a water jet, a drill, etc. In one or more embodiments, a first flat stock 100 may be disposed over a second flat stock 100 and a third flat stock 100 and the first flat stock 100, the second flat stock 100, and the third flat stock 100 may be simultaneously modified by cutting predefined patterns into the first flat stock 100, the second flat stock 100, and the third flat stock 100. Illustratively, modified flat stock 200 may comprise a first flat stock 100 disposed over a second flat stock 100 and a third flat stock 100 wherein the first flat stock 100, the second flat stock 100, and the third flat stock 100 are modified by cutting predefined patterns into the first flat stock 100, the second flat stock 100, and the third flat stock 100, e.g., modified flat stock 200 may comprise a first flat stock 100, a second flat stock 100, and a third flat stock 100 cut by a laser ablation, an electrical discharge machine, a water jet, a drill, etc. In one or more embodiments, modified flat stock 200 may comprise a plurality of tiers of open blunt blank tips 213, e.g., tiers of flat stock 100 may be actuated relative to a tool electrode of an electrical discharge machine to cut out a plurality of tiers of open blunt blank tips 213. For example, tiers of flat stock 100 may be disposed in a plane perpendicular to a tool electrode of an electrical discharge machine and then tiers of flat stock 100 may be actuated relative to the tool electrode to cut out a plurality of open blunt blank tips 213.

FIGS. 3A and 3B are schematic diagrams illustrating a blank base. FIG. 3A illustrates a top view and a side view of a step blank base 300. Illustratively, step blank base 300 may comprise a blank tip shoulder interface 301, a blank proximal end 302, a blank tip interface 340, and a blank base shoulder 350. In one or more embodiments, step blank base 300 may be manufactured from any suitable material, e.g., polymers, metals, metal alloys, etc., or from any combination of suitable materials. Illustratively, step blank base 300 may be manufactured from stainless steel, e.g., step blank base 300 may be manufactured from 17-7 PH Stainless Steel Condition C. FIG. 3B illustrates a top view and a side view of a blunt blank base 305. Illustratively, blunt blank base 305 may comprise a blank proximal end 302 and a blunt blank tip interface 360. In one or more embodiments, blunt blank base 305 may be manufactured from any suitable material, e.g., polymers, metals, metal alloys, etc., or from any combination of suitable materials. Illustratively, blunt blank base 305 may be manufactured from stainless steel, e.g., blunt blank base 305 may be manufactured from 17-7 PH Stainless Steel Condition C.

Figure 4A:
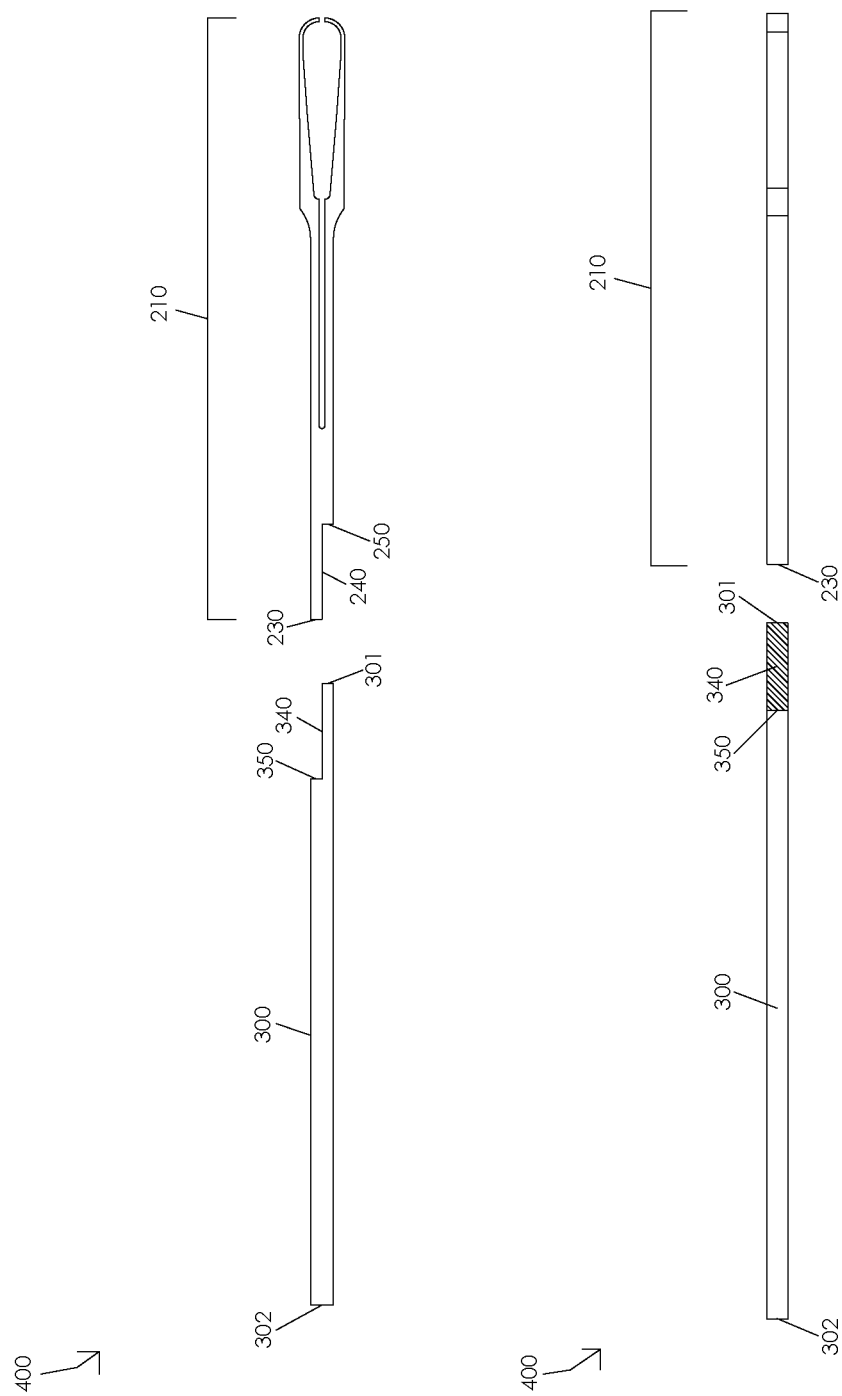

FIGS. 4A, 4B, 4C, and 4D are schematic diagrams illustrating exploded views of a blank assembly 400. FIG. 4A illustrates a top view and a side view of a blank assembly 400. In one or more embodiments, blank assembly 400 may comprise a step blank base 300 and a closed step blank tip 210. Illustratively, a portion of step blank base 300 may be configured to interface with a portion of closed step blank tip 210, e.g., a portion of closed step blank tip 210 may be configured to interface with a portion of step blank base 300. In one or more embodiments, closed step blank tip 210 and step blank base 300 may be disposed wherein blank base shoulder interface 230 abuts blank base shoulder 350. Illustratively, closed step blank tip 210 and step blank base 300 may be disposed wherein blank tip shoulder 250 abuts blank tip shoulder interface 301. In one or more embodiments, closed step blank tip 210 and step blank base 300 may be disposed wherein blank base interface 240 abuts blank tip interface 340.

Figure 4B:
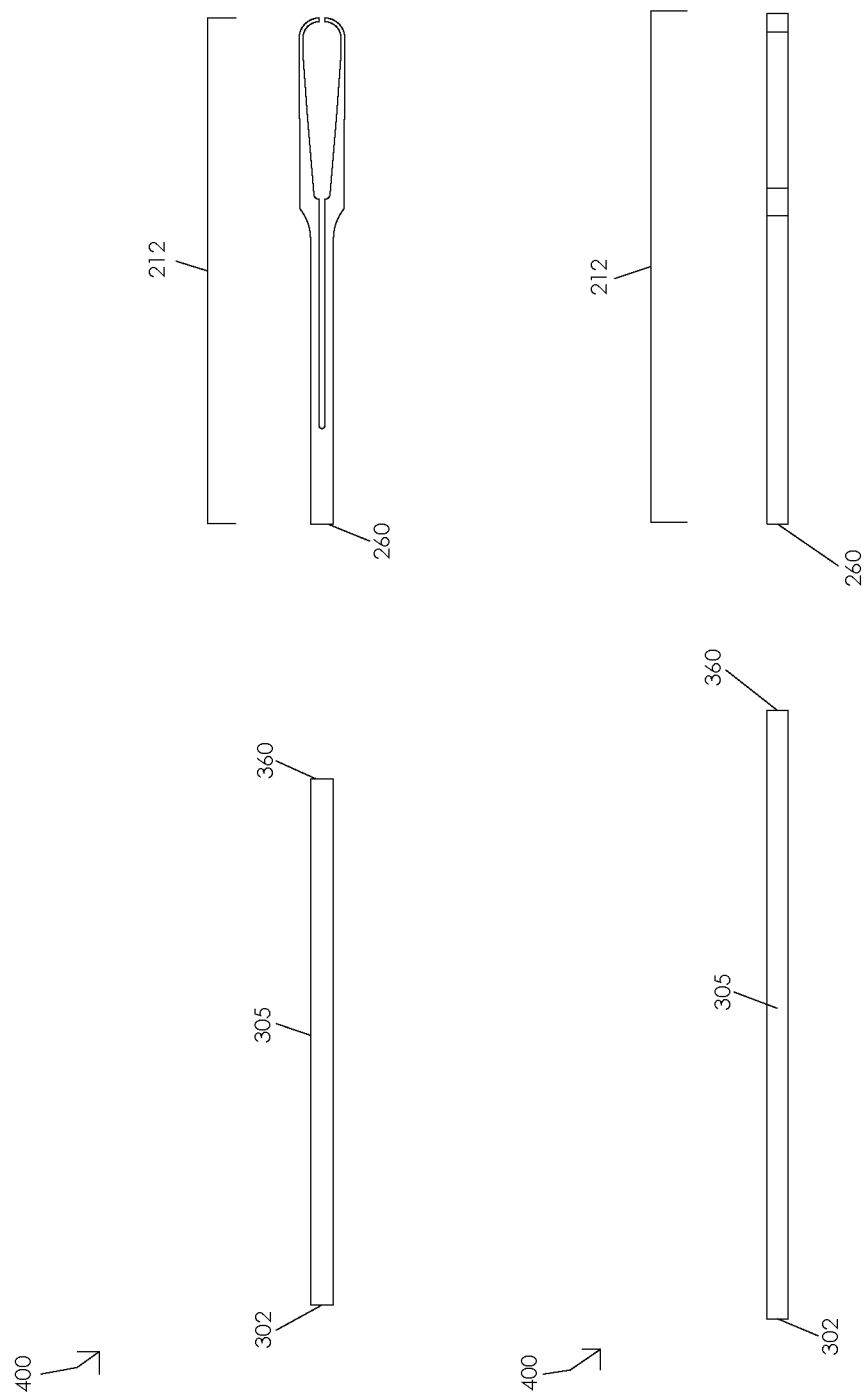

FIG. 4B illustrates a top view and a side view of a blank assembly 400. In one or more embodiments, blank assembly 400 may comprise a blunt blank base 305 and a closed blunt blank tip 212. Illustratively, a portion of blunt blank base 305 may be configured to interface with a portion of closed blunt blank tip 212, e.g., a portion of closed blunt blank tip 212 may be configured to interface with a portion of blunt blank base 305. In one or more embodiments, closed blunt blank tip 212 and blunt blank base 305 may be disposed wherein blunt blank base interface 260 abuts blunt blank tip interface 360.

Figure 4C:
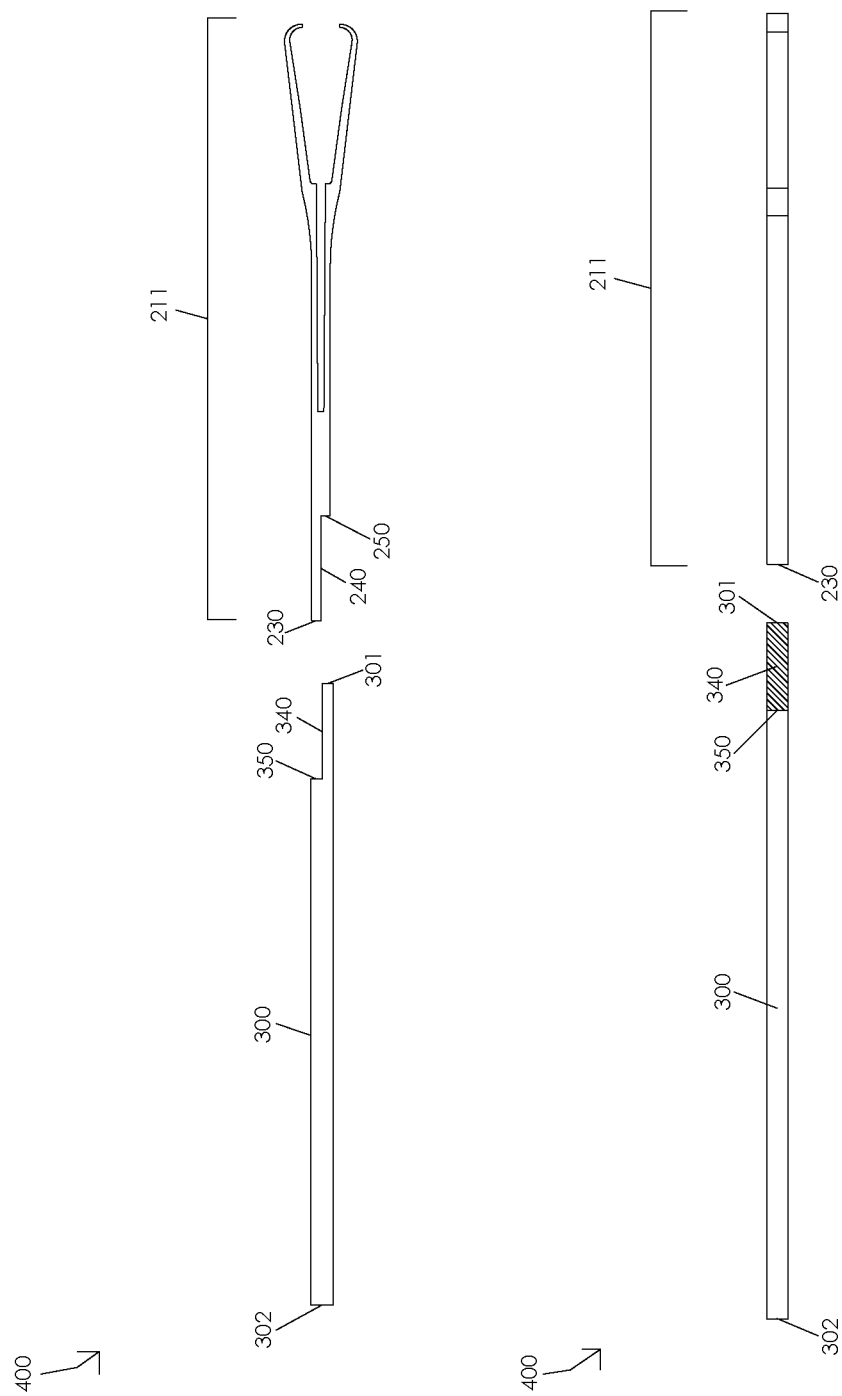

FIG. 4C illustrates a top view and a side view of a blank assembly 400. In one or more embodiments, blank assembly 400 may comprise a step blank base 300 and an open step blank tip 211. Illustratively, a portion of step blank base 300 may be configured to interface with a portion of open step blank tip 211, e.g., a portion of open step blank tip 211 may be configured to interface with a portion of step blank base 300. In one or more embodiments, open step blank tip 211 and step blank base 300 may be disposed wherein blank base shoulder interface 230 abuts blank base shoulder 350. Illustratively, open step blank tip 211 and step blank base 300 may be disposed wherein blank tip shoulder 250 abuts blank tip shoulder interface 301. In one or more embodiments, open step blank tip 210 and step blank base 300 may be disposed wherein blank base interface 240 abuts blank tip interface 340.

FIG. 4D illustrates a top view and a side view of a blank assembly 400. In one or more embodiments, blank assembly 400 may comprise a blunt blank base 305 and an open blunt blank tip 213. Illustratively, a portion of blunt blank base 305 may be configured to interface with a portion of open blunt blank tip 213, e.g., a portion of open blunt blank tip 213 may be configured to interface with a portion of blunt blank base 305. In one or more embodiments, open blunt blank tip 213 and blunt blank base 305 may be disposed wherein blunt blank base interface 260 abuts blunt blank tip interface 360.

Figure 5A:
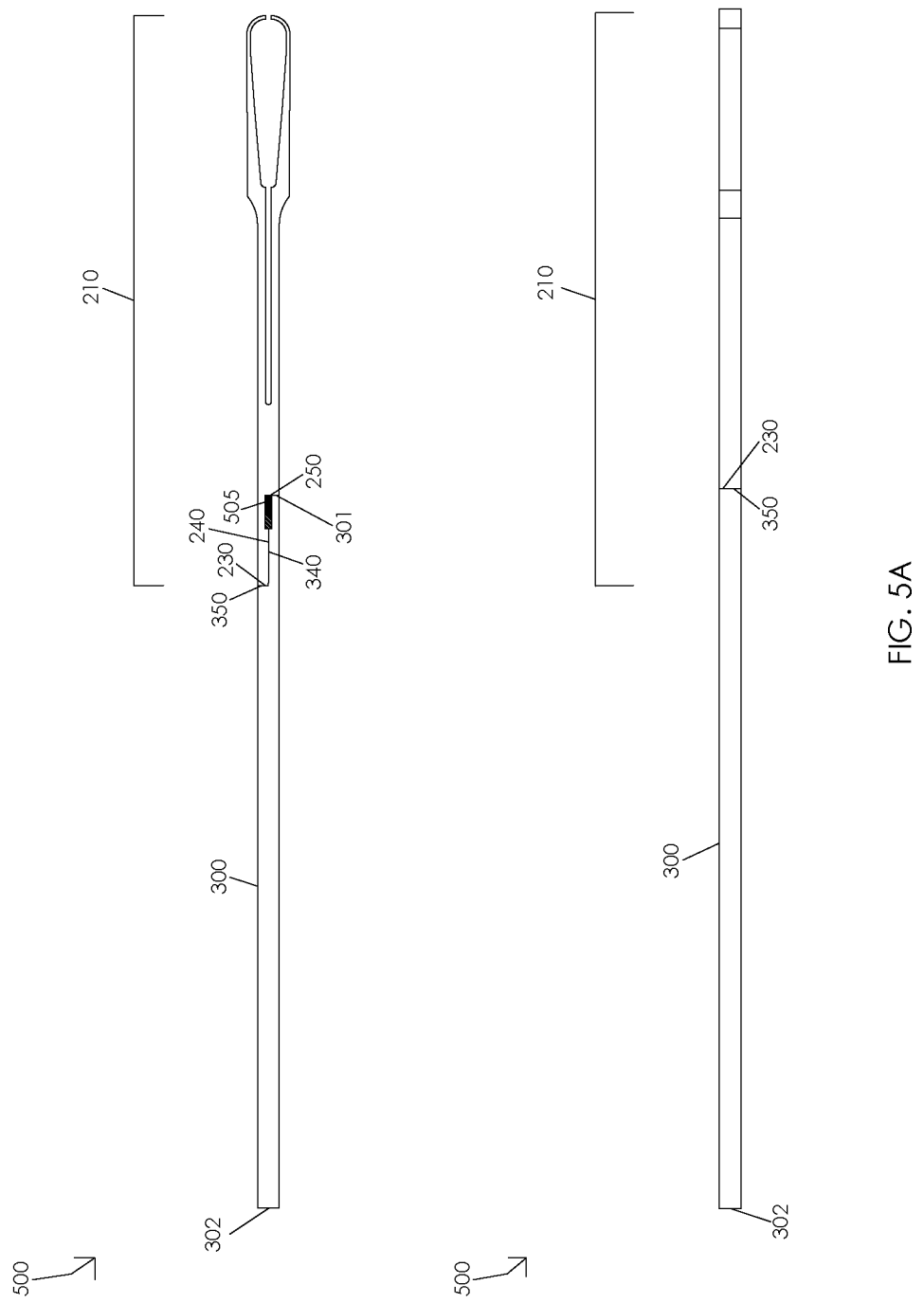
FIGS. 5A, 5B, 5C, and 5D are schematic diagrams illustrating an assembled blank.

FIGS. 5A, 5B, 5C, and 5D are schematic diagrams illustrating an assembled blank 500. FIG. 5A illustrates a top view and a side view of an assembled blank 500. In one or more embodiments, assembled blank 500 may comprise a step blank base 300 fixed to a closed step blank tip 210. Illustratively, blank base shoulder interface 230 may be fixed to blank base shoulder 350. In one or more embodiments, blank base interface 240 may be fixed to blank tip interface 340. Illustratively, blank tip shoulder 250 may be fixed to blank tip shoulder interface 301. In one or more embodiments, step blank base 300 may be fixed to closed step blank tip 210 wherein a first portion of step blank base 300 adjacent to a first portion of closed step blank tip 210 forms a first plane and a second portion of step blank base 300 adjacent to a second portion of closed step blank tip 210 forms a second plane and the first plane is perpendicular to the second plane, e.g., blank base shoulder interface 230 and blank base shoulder 350 may comprise a first plane and blank base interface 240 and blank tip interface 340 may comprise a second plane wherein the first plane is perpendicular to the second plane. Illustratively, blank base interface 240 and blank tip interface 340 may comprise a first plane and blank tip shoulder 250 and blank tip shoulder interface 301 may comprise a second plane wherein the first plane is perpendicular to the second plane. In one or more embodiments, step blank base 300 may be fixed to closed step blank tip 210 wherein a first portion of step blank base 300 adjacent to a first portion of closed step blank tip 210 forms a first plane and a second portion of step blank base 300 adjacent to a second portion of closed step blank tip 210 forms a second plane and the first plane is parallel to the second plane, e.g., blank base shoulder interface 230 and blank base shoulder 350 may comprise a first plane and blank tip shoulder 250 and blank tip shoulder interface 301 may comprise a second plane wherein the first plane is parallel to the second plane. Illustratively, step blank base 300 may be fixed to closed step blank tip 210 wherein a first portion of step blank base 300 adjacent to a first portion of closed step blank tip 210 forms a first plane, a second portion of step blank base 300 adjacent to a second portion of closed step blank tip 210 forms a second plane, and a third portion of step blank base 300 adjacent to a third portion of closed step blank tip 210 forms a third plane and the first plane is parallel to the second plane and the third plane is perpendicular to the first plane and the second plane, e.g., blank base should interface 230 and blank base shoulder 350 may comprise a first plane, blank tip shoulder 250 and blank tip shoulder interface 301 may comprise a second plane, and blank base interface 240 and blank tip interface 340 may comprise a third plane wherein the first plane is parallel to the second plane and the third plane is perpendicular to the first plane and the second plane.

In one or more embodiments, step blank base 300 may be fixed to closed step blank tip 210 by an adhesive or any suitable fixation means, e.g., step blank base 300 may be fixed to closed step blank tip 210 by a press fit. Illustratively, step blank base 300 may be fixed to closed step blank tip 210 by a weld 505, e.g., step blank base 300 may be fixed to closed step blank tip 210 by a laser weld 505. Illustratively, step blank base 300 and closed step blank tip 210 may be welded together by a laser with an operating voltage set in a range of 190 to 210 Volts, e.g., step blank base 300 and closed step blank tip 210 may be welded together by a laser with an operating voltage set at 202 Volts. In one or more embodiments, step blank base 300 and closed step blank tip 210 may be welded together by a laser with an operating voltage set at less than 190 Volts or greater than 210 Volts. Illustratively, step blank base 300 and closed step blank tip 210 may be welded together by a laser with a pulse duration in a range of 0.5 to 2.5 milliseconds, e.g., step blank base 300 and closed step blank tip 210 may be welded together by a laser with a pulse duration of 1.7 milliseconds. In one or more embodiments, step blank base 300 and closed step blank tip 210 may be welded together by a laser with a pulse duration of less than 0.5 milliseconds or greater than 2.5 milliseconds. Illustratively, step blank base 300 and closed step blank tip 210 may be welded together by a laser with a frequency in a range of 1.0 to 5.0 Hz, e.g., step blank base 300 and closed step blank tip 210 may be welded together by a laser with a frequency of 2.5 Hz. In one or more embodiments, step blank base 300 and closed step blank tip 210 may be welded together by a laser with a frequency of less than 1.0 Hz or greater than 5.0 Hz. Illustratively, step blank base 300 and closed step blank tip 210 may be welded together by a laser having a spot diameter in a range of 0.10 to 0.50 millimeters, e.g., step blank base 300 and closed step blank tip 210 may be welded together by a laser having a spot diameter of 0.30 millimeters. In one or more embodiments, step blank base 300 and closed step blank tip 210 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 5B:
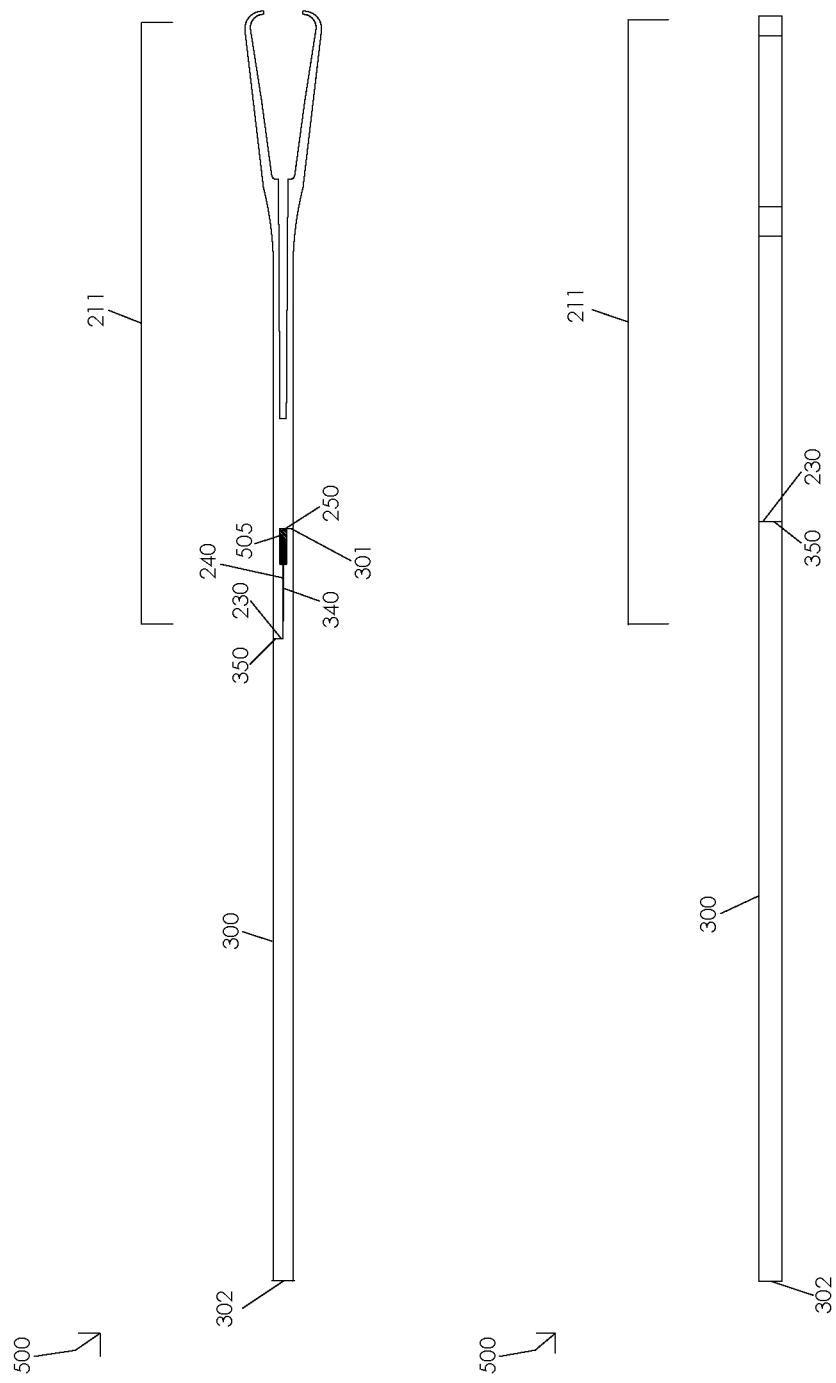

FIG. 5B illustrates a top view and a side view of an assembled blank 500. In one or more embodiments, assembled blank 500 may comprise a step blank base 300 fixed to an open step blank tip 211. Illustratively, blank base shoulder interface 230 may be fixed to blank base shoulder 350. In one or more embodiments, blank base interface 240 may be fixed to blank tip interface 340. Illustratively, blank tip shoulder 250 may be fixed to blank tip shoulder interface 301. In one or more embodiments, step blank base 300 may be fixed to open step blank tip 211 wherein a first portion of step blank base 300 adjacent to a first portion of open step blank tip 211 forms a first plane and a second portion of step blank base 300 adjacent to a second portion of open step blank tip 211 forms a second plane and the first plane is perpendicular to the second plane, e.g., blank base shoulder interface 230 and blank base shoulder 350 may comprise a first plane and blank base interface 240 and blank tip interface 340 may comprise a second plane wherein the first plane is perpendicular to the second plane. Illustratively, blank base interface 240 and blank tip interface 340 may comprise a first plane and blank tip shoulder 250 and blank tip shoulder interface 301 may comprise a second plane wherein the first plane is perpendicular to the second plane. In one or more embodiments, step blank base 300 may be fixed to open step blank tip 211 wherein a first portion of step blank base 300 adjacent to a first portion of open step blank tip 211 forms a first plane and a second portion of step blank base 300 adjacent to a second portion of open step blank tip 211 forms a second plane and the first plane is parallel to the second plane, e.g., blank base shoulder interface 230 and blank base shoulder 350 may comprise a first plane and blank tip shoulder 250 and blank tip shoulder interface 301 may comprise a second plane wherein the first plane is parallel to the second plane. Illustratively, step blank base 300 may be fixed to open step blank tip 211 wherein a first portion of step blank base 300 adjacent to a first portion of open step blank tip 211 forms a first plane, a second portion of step blank base 300 adjacent to a second portion of open step blank tip 211 forms a second plane, and a third portion of step blank base 300 adjacent to a third portion of open step blank tip 211 forms a third plane and the first plane is parallel to the second plane and the third plane is perpendicular to the first plane and the second plane, e.g., blank base should interface 230 and blank base shoulder 350 may comprise a first plane, blank tip shoulder 250 and blank tip shoulder interface 301 may comprise a second plane, and blank base interface 240 and blank tip interface 340 may comprise a third plane wherein the first plane is parallel to the second plane and the third plane is perpendicular to the first plane and the second plane.

In one or more embodiments, step blank base 300 may be fixed to open step blank tip 211 by an adhesive or any suitable fixation means, e.g., step blank base 300 may be fixed to open step blank tip 211 by a press fit. Illustratively, step blank base 300 may be fixed to open step blank tip 211 by a weld 505, e.g., step blank base 300 may be fixed to open step blank tip 211 by a laser weld 505. Illustratively, step blank base 300 and open step blank tip 211 may be welded together by a laser with an operating voltage set in a range of 190 to 210 Volts, e.g., step blank base 300 and open step blank tip 211 may be welded together by a laser with an operating voltage set at 202 Volts. In one or more embodiments, step blank base 300 and open step blank tip 211 may be welded together by a laser with an operating voltage set at less than 190 Volts or greater than 210 Volts. Illustratively, step blank base 300 and open step blank tip 211 may be welded together by a laser with a pulse duration in a range of 0.5 to 2.5 milliseconds, e.g., step blank base 300 and open step blank tip 211 may be welded together by a laser with a pulse duration of 1.7 milliseconds. In one or more embodiments, step blank base 300 and open step blank tip 211 may be welded together by a laser with a pulse duration of less than 0.5 milliseconds or greater than 2.5 milliseconds. Illustratively, step blank base 300 and open step blank tip 211 may be welded together by a laser with a frequency in a range of 1.0 to 5.0 Hz, e.g., step blank base 300 and open step blank tip 211 may be welded together by a laser with a frequency of 2.5 Hz. In one or more embodiments, step blank base 300 and open step blank tip 211 may be welded together by a laser with a frequency of less than 1.0 Hz or greater than 5.0 Hz. Illustratively, step blank base 300 and open step blank tip 211 may be welded together by a laser having a spot diameter in a range of 0.10 to 0.50 millimeters, e.g., step blank base 300 and open step blank tip 211 may be welded together by a laser having a spot diameter of 0.30 millimeters. In one or more embodiments, step blank base 300 and open step blank tip 211 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 5C:
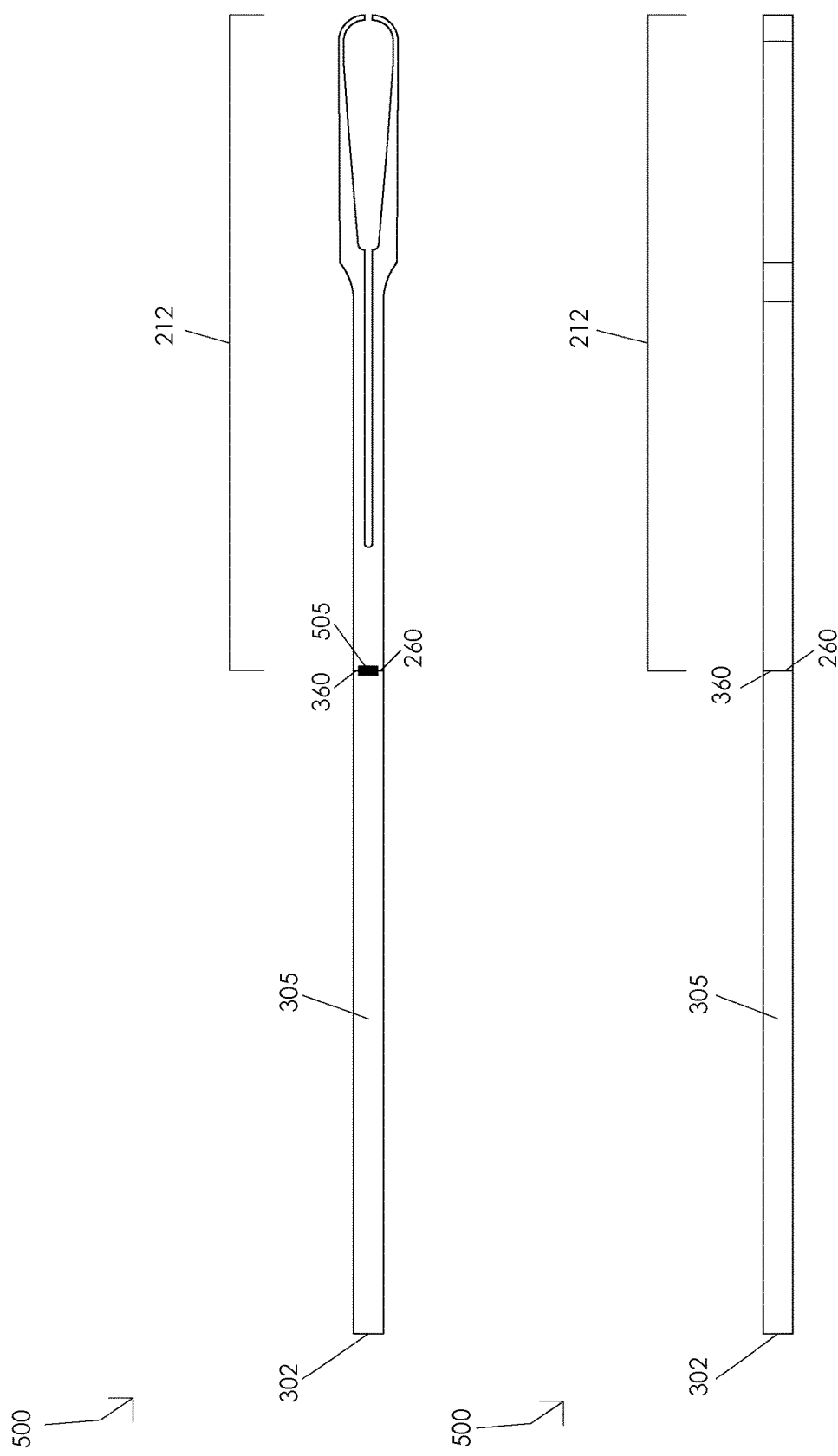

FIG. 5C illustrates a top view and a side view of an assembled blank 500. In one or more embodiments, assembled blank 500 may comprise a blunt blank base 305 fixed to a closed blunt blank tip 212. Illustratively, blunt blank base interface 260 may be fixed to blunt blank tip interface 360. In one or more embodiments, blunt blank base 305 may be fixed to closed blunt blank tip 212 by an adhesive or any suitable fixation means, e.g., blunt blank base 305 may be fixed to closed blunt blank tip 212 by a press fit. Illustratively, blunt blank base 305 may be fixed to closed blunt blank tip 212 by a weld 505, e.g., blunt blank base 305 may be fixed to closed blunt blank tip 212 by a laser weld 505. Illustratively, blunt blank base 305 and closed blunt blank tip 212 may be welded together by a laser with an operating voltage set in a range of 190 to 210 Volts, e.g., blunt blank base 305 and closed blunt blank tip 212 may be welded together by a laser with an operating voltage set at 202 Volts. In one or more embodiments, blunt blank base 305 and closed blunt blank tip 212 may be welded together by a laser with an operating voltage set at less than 190 Volts or greater than 210 Volts. Illustratively, blunt blank base 305 and closed blunt blank tip 212 may be welded together by a laser with a pulse duration in a range of 0.5 to 2.5 milliseconds, e.g., blunt blank base 305 and closed blunt blank tip 212 may be welded together by a laser with a pulse duration of 1.7 milliseconds. In one or more embodiments, blunt blank base 305 and closed blunt blank tip 212 may be welded together by a laser with a pulse duration of less than 0.5 milliseconds or greater than 2.5 milliseconds. Illustratively, blunt blank base 305 and closed blunt blank tip 212 may be welded together by a laser with a frequency in a range of 1.0 to 5.0 Hz, e.g., blunt blank base 305 and closed blunt blank tip 212 may be welded together by a laser with a frequency of 2.5 Hz. In one or more embodiments, blunt blank base 305 and closed blunt blank tip 212 may be welded together by a laser with a frequency of less than 1.0 Hz or greater than 5.0 Hz. Illustratively, blunt blank base 305 and closed blunt blank tip 212 may be welded together by a laser having a spot diameter in a range of 0.10 to 0.50 millimeters, e.g., blunt blank base 305 and closed blunt blank tip 212 may be welded together by a laser having a spot diameter of 0.30 millimeters. In one or more embodiments, blunt blank base 305 and closed blunt blank tip 212 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 5D:
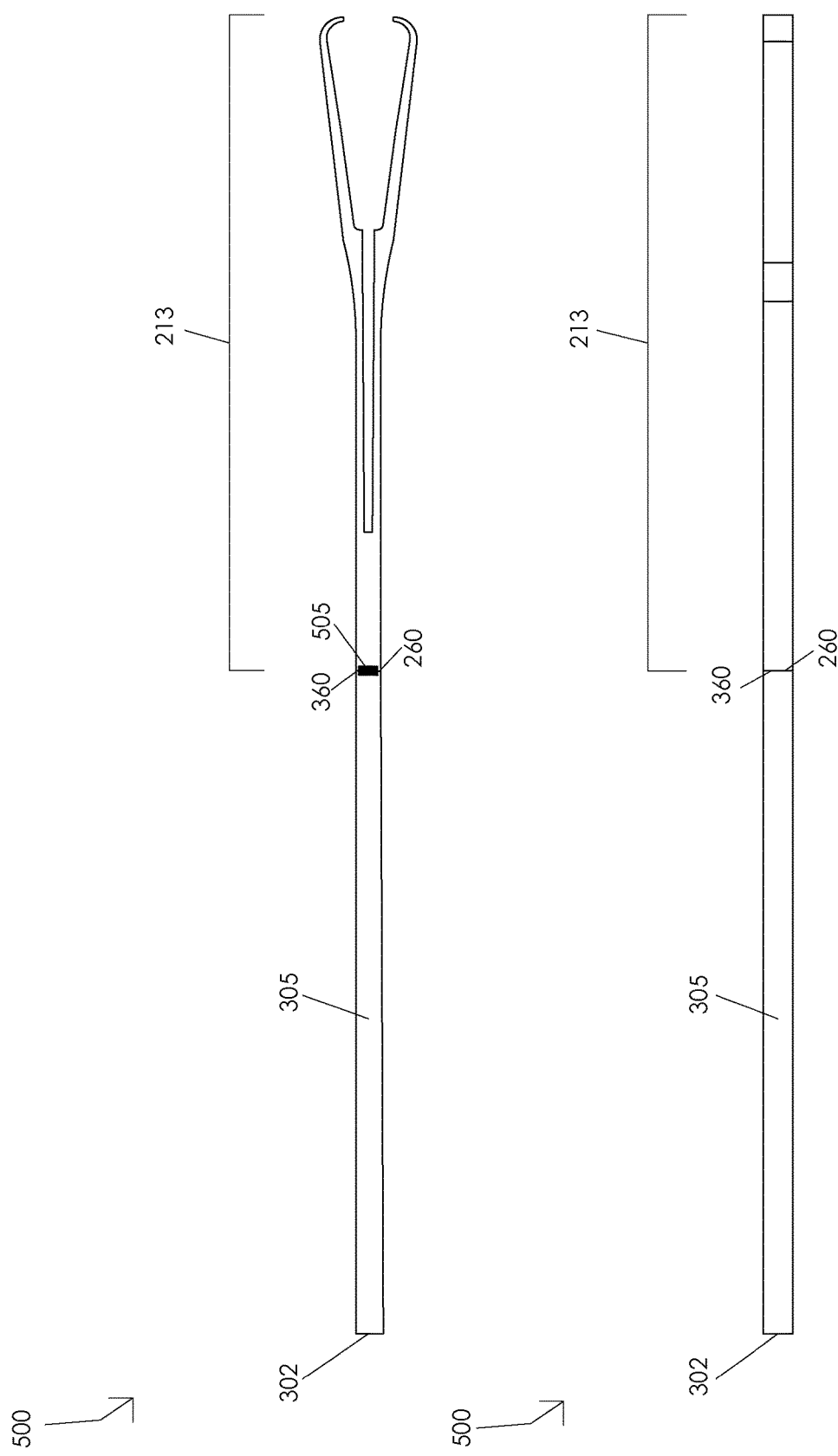

FIG. 5D illustrates a top view and a side view of an assembled blank 500. In one or more embodiments, assembled blank 500 may comprise a blunt blank base 305 fixed to an open blunt blank tip 213. Illustratively, blunt blank base interface 260 may be fixed to blunt blank tip interface 360. In one or more embodiments, blunt blank base 305 may be fixed to closed blunt blank tip 212 by an adhesive or any suitable fixation means, e.g., blunt blank base 305 may be fixed to open blunt blank tip 213 by a press fit. Illustratively, blunt blank base 305 may be fixed to open blunt blank tip 213 by a weld 505, e.g., blunt blank base 305 may be fixed to open blunt blank tip 213 by a laser weld 505. Illustratively, blunt blank base 305 and open blunt blank tip 213 may be welded together by a laser with an operating voltage set in a range of 190 to 210 Volts, e.g., blunt blank base 305 and open blunt blank tip 213 may be welded together by a laser with an operating voltage set at 202 Volts. In one or more embodiments, blunt blank base 305 and open blunt blank tip 213 may be welded together by a laser with an operating voltage set at less than 190 Volts or greater than 210 Volts. Illustratively, blunt blank base 305 and open blunt blank tip 213 may be welded together by a laser with a pulse duration in a range of 0.5 to 2.5 milliseconds, e.g., blunt blank base 305 and open blunt blank tip 213 may be welded together by a laser with a pulse duration of 1.7 milliseconds. In one or more embodiments, blunt blank base 305 and open blunt blank tip 213 may be welded together by a laser with a pulse duration of less than 0.5 milliseconds or greater than 2.5 milliseconds. Illustratively, blunt blank base 305 and open blunt blank tip 213 may be welded together by a laser with a frequency in a range of 1.0 to 5.0 Hz, e.g., blunt blank base 305 and open blunt blank tip 213 may be welded together by a laser with a frequency of 2.5 Hz. In one or more embodiments, blunt blank base 305 and open blunt blank tip 213 may be welded together by a laser with a frequency of less than 1.0 Hz or greater than 5.0 Hz. Illustratively, blunt blank base 305 and open blunt blank tip 213 may be welded together by a laser having a spot diameter in a range of 0.10 to 0.50 millimeters, e.g., blunt blank base 305 and open blunt blank tip 213 may be welded together by a laser having a spot diameter of 0.30 millimeters. In one or more embodiments, blunt blank base 305 and open blunt blank tip 213 may be welded together by a laser having a spot diameter of less than 0.10 millimeters or greater than 0.50 millimeters.

Illustratively, weld 505 may comprise a single laser weld on a top side of assembled blank 500. In one or more embodiments, weld 505 may comprise a single laser weld on a top side of assembled blank 500 and a single laser weld on a bottom side of assembled blank 500. Illustratively, weld 505 may comprise a plurality of laser welds on a top side of assembled blank 500. In one or more embodiments, weld 505 may comprise a plurality of laser welds on a top side of assembled blank 500 and a plurality of laser welds on a bottom side of assembled blank 500. Illustratively, weld 505 may comprise six laser welds on a top side of assembled blank 500 and six laser welds on a bottom side of assembled blank 500.

Figure 6:
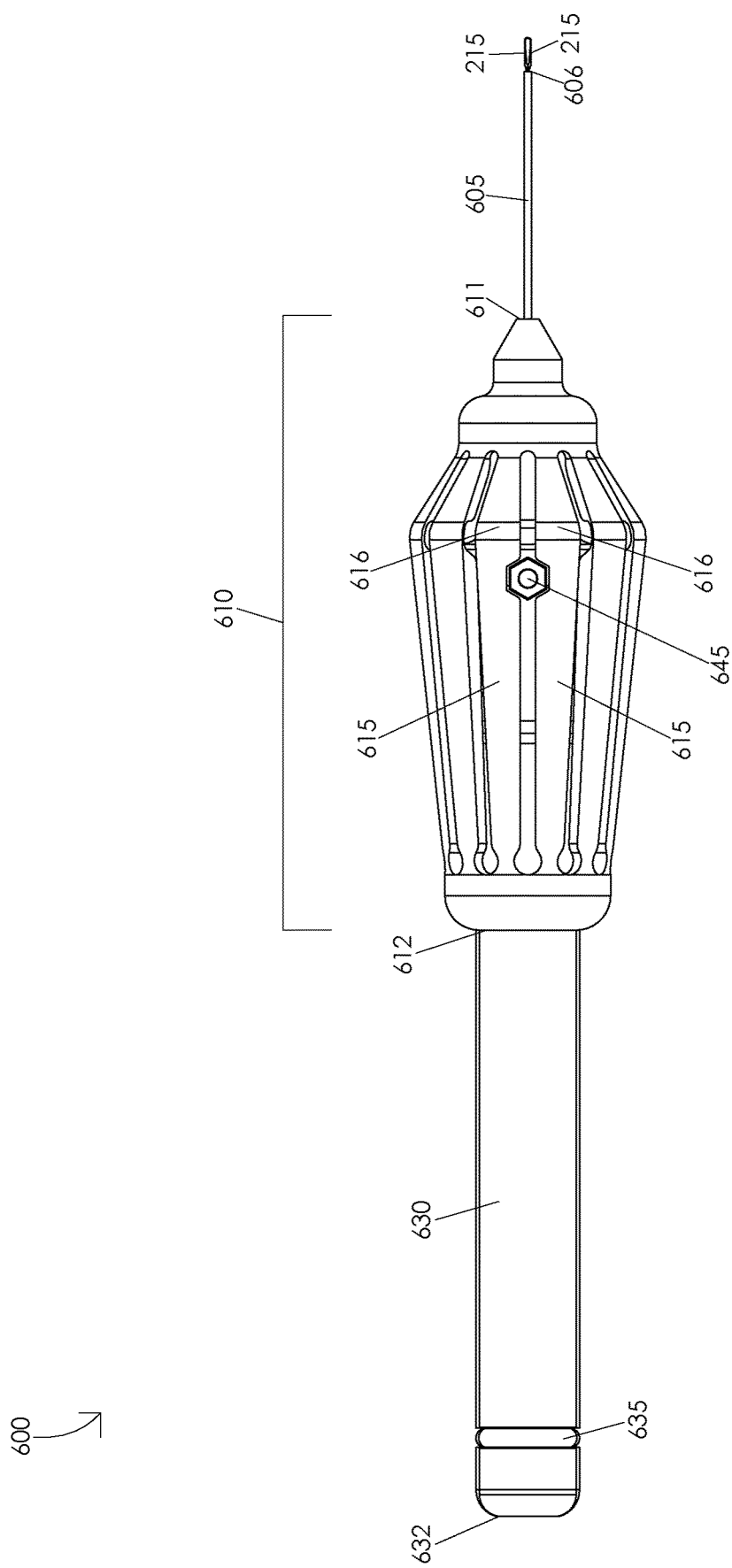
FIG. 6 is a schematic diagram illustrating a microsurgical instrument.

FIG. 6 is a schematic diagram illustrating a microsurgical instrument 600. In one or more embodiments, microsurgical instrument 600 may comprises a hypodermic tube 605, an actuation structure 610, and an end stick 630. Illustratively, actuation structure 610 may comprise an actuation structure distal end 611, an actuation structure proximal end 612, and a plurality of actuation arms 615. In one or more embodiments, each actuation arm 615 of a plurality of actuation arms 615 may comprise an extension mechanism 616. Illustratively, actuation structure distal end 611 may extend a decompressed distance from actuation structure proximal end 612, e.g., when actuation structure 610 comprises a decompressed actuation structure 610. In one or more embodiments, a decompressed distance may be in a range of 1.6 to 3.0 inches, e.g., a decompressed distance may be 2.25 inches. Illustratively, a decompressed distance may be less than 1.6 inches or greater than 3.0 inches. In one or more embodiments, actuation structure 610 may be manufactured from any suitable material, e.g., polymers, metals, metal alloys, etc., or from any combination of suitable materials. Illustratively, actuation structure 610 may be manufactured from a shape memory material. In one or more embodiments, actuation structure 610 may be manufactured using a selective laser sintering machine. Illustratively, actuation structure 610 may be manufactured by additive manufacturing or 3D printing. In one or more embodiments, actuation structure 610 may be manufactured from a material suitable for sterilization by a medical autoclave. Illustratively, actuation structure 610 may be manufactured from a material, e.g., Nylon, configured to withstand exposure to temperatures, pressures, and ambient conditions present in a medical autoclave without degradation. For example, actuation structure 610 may be configured to function normally after exposure in a temperature 250° F. for 15 minutes at an atmospheric pressure of 15 psi. In one or more embodiments, actuation structure 610 may be configured to be used in a surgical procedure and then sterilized by a medical autoclave at least three times. Illustratively, actuation structure 610 may be configured to be used in a surgical procedure and then sterilized by a medical autoclave more than three times.

In one or more embodiments, actuation structure 610 may have a density in a range of 0.02 to 0.06 pounds per cubic inch, e.g., actuation structure 610 may have a density of 0.042 pounds per cubic inch. Illustratively, actuation structure 610 may have a density less than 0.02 pounds per cubic inch or greater than 0.06 pounds per cubic inch. In one or more embodiments, actuation structure 610 may have a mass in a range of 0.005 to 0.025 pounds, e.g., actuation structure 610 may have a mass of 0.015 pounds. Illustratively, actuation structure 610 may have a mass less than 0.005 pounds or greater than 0.025 pounds. In one or more embodiments, actuation structure 610 may have a volume in a range of 0.2 to 0.5 cubic inches, e.g., actuation structure 610 may have a volume of 0.359 cubic inches. Illustratively, actuation structure 610 may have a volume less than 0.2 cubic inches or greater than 0.5 cubic inches. In one or more embodiments, actuation structure 610 may have a surface area in a range of 7.5 to 13.0 square inches, e.g., actuation structure 610 may have a surface area of 10.8 square inches. Illustratively, actuation structure 610 may have a surface area less than 7.5 square inches or greater than 13.0 square inches.

In one or more embodiments, actuation structure 610 may be configured to project actuation structure distal end 611 a first distance from actuation structure proximal end 612, e.g., when actuation structure 610 is fully decompressed. Illustratively, actuation structure 610 may comprise a shape memory material configured to project actuation structure distal end 611 a second distance from actuation structure proximal end 612, e.g., when actuation structure 610 is fully compressed. In one or more embodiments, the second distance from actuation structure proximal end 612 may be greater than the first distance from actuation structure proximal end 612. Illustratively, a compression of actuation structure 610 may be configured to gradually extend actuation structure distal end 611 relative to actuation structure proximal end 612. In one or more embodiments, actuation structure distal end 611 may extend a compressed distance from actuation structure proximal end 612, e.g., when actuation structure 610 comprises a compressed actuation structure 610. Illustratively, a compressed distance may be a distance in a range of 1.6 to 3.0 inches, e.g., a compressed distance may be 2.29 inches. In one or more embodiments, a compressed distance may be less than 1.6 inches or greater than 3.0 inches. Illustratively, a compressed distance may be in a range of 0.02 to 0.05 inches greater than a decompressed distance. In one or more embodiments, a compressed distance may be less than 0.02 inches greater than a decompressed distance. Illustratively, a compressed distance may be more than 0.05 inches greater than a decompressed distance. In one or more embodiments, a compressed distance may be in a range of 1.0 to 2.0 percent greater than a decompressed distance. Illustratively, a compressed distance may be less than 1.0 percent greater than a decompressed distance. In one or more embodiments, a compressed distance may be more than 2.0 percent greater than a decompressed distance.

Illustratively, actuation structure 610 may be compressed by an application of a force, e.g., a compressive force, to a portion of actuation structure 610. In one or more embodiments, an application of a compressive force in a range of 100 to 300 grams may be configured to compress actuation structure 610, e.g., an application of a compressive force of 200 grams may be configured to compress actuation structure 610. Illustratively, an application of a compressive force of less than 100 grams or greater than 300 grams may be configured to compress actuation structure 610. In one or more embodiments, actuation structure 610 may be compressed by an application of one or more compressive forces at one or more locations around an outer perimeter of actuation structure 610. Illustratively, the one or more locations may comprise any particular locations of a plurality of locations around an outer perimeter of actuation structure 610. For example, a surgeon may compress actuation structure 610 by squeezing actuation structure 610. Illustratively, a surgeon may compress actuation structure 610 by squeezing actuation structure 610 at any particular location of a plurality of locations around an outer perimeter of actuation structure 610. In one or more embodiments, a surgeon may compress actuation structure 610 by applying a force to a portion of actuation structure 610, e.g., when actuation structure 610 is in a first rotational orientation. Illustratively, the surgeon may then rotate actuation structure 610 and compress actuation structure 610 by applying a force to a portion of actuation structure 610, e.g., when actuation structure 610 is in a second rotational orientation. In one or more embodiments, the surgeon may then rotate actuation structure 610 and compress actuation structure 610 by applying a force to a portion of actuation structure 610, e.g., when actuation structure 610 is in a third rotational orientation. Illustratively, a surgeon may compress actuation structure 610 by applying a force to a portion of actuation structure 610, e.g., when actuation structure 610 is in any rotational orientation.

In one or more embodiments, actuation structure 610 may be compressed by an application of a compressive force to any one or more actuation arms 615 of a plurality of actuation arms 615. Illustratively, each actuation arm 615 may be connected to one or more actuation arms 615 of a plurality of actuation arms 615 wherein an actuation of a particular actuation arm 615 may be configured to actuate every actuation arm 615 of a plurality of actuation arms 615. In one or more embodiments, one or more actuation arms 615 may be configured to actuate in pairs or groups. For example, an actuation of a first actuation arm 615 may be configured to actuate a second actuation arm 615. Illustratively, a compression of actuation structure 610, e.g., due to an application of a force to a portion of actuation structure 610, may be configured to expand an extension mechanism 616 of a particular actuation arm 110. In one or more embodiments, an expansion of an extension mechanism 616 of a particular actuation arm 615 may be configured to increase a distance between a distal end and a proximal end of the particular actuation arm 615. Illustratively, an expansion of an extension mechanism 616 of a particular actuation arm 615 may be configured to expand an extension mechanism 616 of every actuation arm 615 of a plurality of actuation arms 615. In one or more embodiments, an expansion of an extension mechanism 616 of every actuation arm 615 of a plurality of actuation arms 615 may be configured to increase a distance between actuation structure distal end 611 and actuation structure proximal end 612. Illustratively, a decompression of actuation structure 610, e.g., due to a reduction of a force applied to a portion of actuation structure 610, may be configured to collapse an extension mechanism 616 of a particular actuation arm 615. In one or more embodiments, a collapse of an extension mechanism 616 of a particular actuation arm 615 may be configured to decrease a distance between a distal end and a proximal end of the particular actuation arm 615. Illustratively, a collapse of an extension mechanism 616 of a particular actuation arm 615 may be configured to collapse an extension mechanism 616 of every actuation arm 615 of a plurality of actuation arms 615. In one or more embodiments, a collapse of an extension mechanism 616 of every actuation arm 615 of a plurality of actuation arms 615 may be configured to decrease a distance between actuation structure distal end 611 and actuation structure proximal end 612.

Illustratively, end stick 630 may comprise an end stick distal end, an end stick proximal end 632, and an identification marker 635. In one or more embodiments, end stick 630 may be fixed to a portion of actuation structure 610, e.g., a portion of end stick 630 may be disposed within actuation structure 610. Illustratively, identification marker 635 may be configured to convey information about microsurgical instrument 600, e.g., identification marker 635 may comprise a color configured to correspond to a particular assembled blank 500. In one or more embodiments, identification marker 635 may comprise a color configured to correspond to a particular size of assembled blank 500. Illustratively, hypodermic tube 605 may comprise a hypodermic tube distal end 606 and a hypodermic tube proximal end. In one or more embodiments, hypodermic tube 605 may be fixed to actuation structure 610, e.g., a portion of hypodermic tube 605 may be disposed within actuation structure 610. Illustratively, assembled blank 500 may be disposed within hypodermic tube 605 and actuation structure 610, e.g., assembled blank 500 may be disposed within hypodermic tube 605 wherein first forceps jaw distal end 216 extends out from hypodermic tube distal end 606 and second forceps jaw distal end 216 extends out from hypodermic tube distal end 606. In one or more embodiments, assembled blank 500 may be fixed within actuation structure 610, e.g., fixation mechanism 645 may be configured to fix a portion of assembled blank 500 within actuation structure 610. For example, fixation mechanism 645 may comprise a setscrew. Illustratively, a portion of assembled blank 500 may be fixed within actuation structure 610 by an adhesive or any suitable fixation means, e.g., a portion of assembled blank 500 may be fixed within actuation structure 610 by a friction fit, a weld, a tie, etc.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument tip, the teachings of the present invention are equally suitable to any systems where the functionality may be employed. Therefore, it is the object of the appended claims to cover all such variations and modifications as come within the true spirit and scope of the invention.

What is claimed is:

1. An instrument tip for an ophthalmic microsurgical instrument having an actuation structure, comprising:
    a blank tip formed of an electric discharge machine modified flat stock, the blank tip having a blank tip distal end and a blank tip proximal end;
    a first forceps jaw of the blank tip having a first forceps jaw distal end and a first forceps jaw proximal end;
    a second forceps jaw of the blank tip having a second forceps jaw distal end and a second forceps jaw proximal end;
    a blank tip aperture of the blank tip;
    a blank base having a blank base distal end and a blank base proximal end wherein the blank base distal end is fixed to the blank tip proximal end by a laser weld to form an assembled blank; and
    wherein at least a portion of the assembled blank is configured for engagement with the actuation structure for actuation of the first forceps jaw and the second forceps jaw between an open position and a closed position.

2. The instrument tip of claim 1 wherein the first forceps jaw distal end is separated from the second forceps jaw distal end by a distance in a range of 0.001 to 0.005 inches.

3. The instrument tip of claim 1 wherein the first forceps jaw distal end is separated from the second forceps jaw distal end by a distance in a range of 0.01 to 0.05 inches.

4. The instrument tip of claim 1 wherein the blank tip and the blank base are manufactured from stainless steel.

5. The instrument tip of claim 1 further comprising:
    the actuation structure having an actuation structure distal end and an actuation structure proximal end;
    a plurality of actuation arms of the actuation structure wherein each actuation arm of the plurality of actuation arms has an extension mechanism; and
    a hypodermic tube extending from the distal end of the actuation structure wherein the blank base is disposed within the hypodermic tube and the actuation structure.

6. The instrument tip of claim 5 further comprising:
    an end stick having an end stick distal end and an end stick proximal end, the end stick partially disposed within the actuation structure.

7. An instrument tip for an ophthalmic microsurgical instrument having an actuation structure, comprising:
    a blank tip formed of an electric discharge machine modified flat stock, the blank tip having a blank tip distal end and a blank tip proximal end;
    a first forceps jaw of the blank tip having a first forceps jaw distal end and a first forceps jaw proximal end;
    a second forceps jaw of the blank tip having a second forceps jaw distal end and a second forceps jaw proximal end;
    a separation distance separating the first forceps distal end and the second forceps jaw distal end;
    a blank tip aperture of the blank tip; and
    wherein at least a portion of the blank tip is configured for engagement with the actuation structure for actuation of the first forceps jaw and the second forceps jaw between an open position and a closed position.

8. The instrument tip of claim 7 wherein the first forceps jaw distal end is separated from the second forceps jaw distal end by a distance in a range of 0.001 to 0.005 inches.

9. The instrument tip of claim 7 wherein the first forceps jaw distal end is separated from the second forceps jaw distal end by a distance in a range of 0.01 to 0.05 inches.

10. The instrument tip of claim 7 wherein the blank tip is manufactured from stainless steel.

11. The instrument tip of claim 7 further comprising:
the actuation structure having an actuation structure distal end and an actuation structure proximal end;
a plurality of actuation arms of the actuation structure wherein each actuation arm of the plurality of actuation arms has an extension mechanism; and
a hypodermic tube extending from the distal end of the actuation structure wherein the blank tip is at least partially disposed in the hypodermic tube.

12. The instrument tip of claim 11 further comprising:
an end stick having an end stick distal end and an end stick proximal end, the end stick partially disposed within the actuation structure.

13. The instrument tip of claim 7 wherein the flat stock has a flat stock thickness in a range of 0.005 to 0.013 inches.

14. The instrument tip of claim 7 wherein the pre-defined pattern is cut into the flat stock by an electrical discharge machine.

15. An instrument tip for an ophthalmic microsurgical instrument, comprising:
a blank tip formed of an electric discharge machine modified flat stock having a blank tip distal end and a blank tip proximal end;
a first forceps jaw of the blank tip having a first forceps jaw distal end and a first forceps jaw proximal end;
a second forceps jaw of the blank tip having a second forceps jaw distal end and a second forceps jaw proximal end;
a separation distance separating the first forceps distal end and the second forceps jaw distal end;
a blank tip aperture of the blank tip; and
wherein at least a portion of the blank tip is configured for actuation of the first forceps jaw and the second forceps jaw to increase or decrease the separation distance.

16. The instrument tip of claim 15 wherein the first forceps jaw distal end is separated from the second forceps jaw distal end by a distance in a range of 0.001 to 0.005 inches.

17. The instrument tip of claim 15 wherein the first forceps jaw distal end is separated from the second forceps jaw distal end by a distance in a range of 0.01 to 0.05 inches.

18. The instrument tip of claim 15 wherein the flat stock has a flat stock thickness in a range of 0.005 to 0.013 inches.

19. The instrument tip of claim 15 wherein the blank tip is manufactured from stainless steel.

20. The instrument tip of claim 15 further comprising:
an actuation structure having an actuation structure distal end and an actuation structure proximal end;
a plurality of actuation arms of the actuation structure wherein each actuation arm of the plurality of actuation arms has an extension mechanism; and
a hypodermic tube extending from the distal end of the actuation structure wherein the blank tip is at least partially disposed in the hypodermic tube.

* * * * *